(12) United States Patent
Shackney et al.

(10) Patent No.: US 7,563,620 B2
(45) Date of Patent: Jul. 21, 2009

(54) CELL AGGREGATE CORRECTION METHOD

(75) Inventors: Stanley E. Shackney, Pittsburgh, PA (US); Charles Smith, Pittsburgh, PA (US); Agnese Pollice, Pittsburgh, PA (US); Kathryn Brown, Eighty Four, PA (US); Deborah Kociban, Pittsburgh, PA (US)

(73) Assignee: Allegheny-Singer Research Institute, Pittsburgh, PA (US)

( * ) Notice: Subject to any disclaimer, the term of this patent is extended or adjusted under 35 U.S.C. 154(b) by 856 days.

(21) Appl. No.: 10/461,018

(22) Filed: Jun. 13, 2003

(65) Prior Publication Data

US 2004/0253738 A1    Dec. 16, 2004

(51) Int. Cl.
*G01N 33/00* (2006.01)
(52) U.S. Cl. .......................................... 436/63; 422/73
(58) Field of Classification Search ................... 422/73; 436/63
See application file for complete search history.

(56) References Cited

U.S. PATENT DOCUMENTS 5,885,840 A * 3/1999 Kamentsky et al. ........... 436/63

OTHER PUBLICATIONS

Schackney, A suitable method for identifying cell aggregates in laser scanning cytometry listmode data for analyzing disaggregated cell suspensions obtained from humcan cancers, Apr. 13, 2004, Cytometry Part B: Clinical Cytometry, vol. 59 B, Issue 1, pp. 10-23.*
CompuCyte, "Laser Scanning Cytometry", 2002, Compucyte, www.compuscyte.com.*
Grace "The Use of Laser Scanning Cytometry to Assess Depth of Penetration of Adenovirus p53 Gene Therapy in Human Xenograft Biopsies." 1999.*

* cited by examiner

*Primary Examiner*—Sam P Siefke
(74) *Attorney, Agent, or Firm*—Ansel M. Schwartz

(57) ABSTRACT

An apparatus for correcting for cell aggregates in a cell suspension from patients. The apparatus includes a laser cytometry scanning mechanism for scanning cells of a sample of a cell suspension to obtain data about the samples patients. The apparatus includes a memory for storing the data, the memory in communication with the scanning mechanism patients. The apparatus includes a computer for identifying in the data cell aggregates in the samples from the samples that have been scanned with an APT function, the computer in communication with the memory. A method for correcting for cell aggregates in a cell suspension from patients with an APT function. A method for correcting for cell aggregates in a cell suspension from patients with up to 98.6% accuracy. A computer readable medium.

7 Claims, 15 Drawing Sheets

50μ ⊢―――――――――――――――――――――⊣

TRUE SINGLETS BY SADDLE FUNCTION

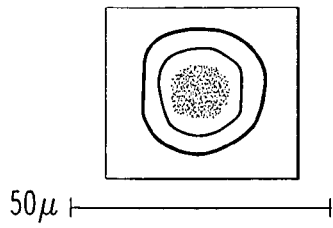
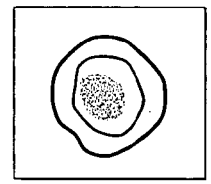
50μ ⊢————————⊣
FIG.1A          FIG.1B
TRUE SINGLETS BY SADDLE FUNCTION
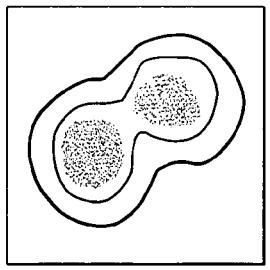
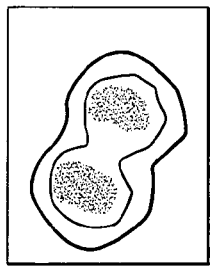
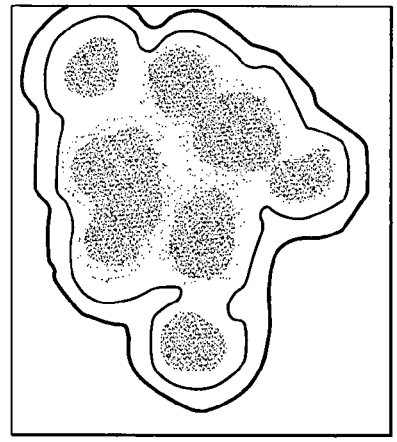
FIG.1C          FIG.1D          FIG.1E
TRUE AGGREGATES BY SADDLE FUNCTION
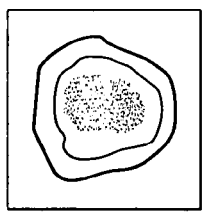
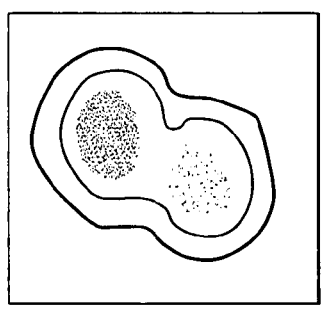
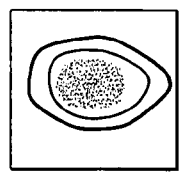
FIG.1F          FIG.1G          FIG.1H
FALSE NEGATIVE AGGREGATES BY     FALSE POSITIVE AGGREGATE
SADDLE FUNCTION                  BY SADDLE FUNCTION

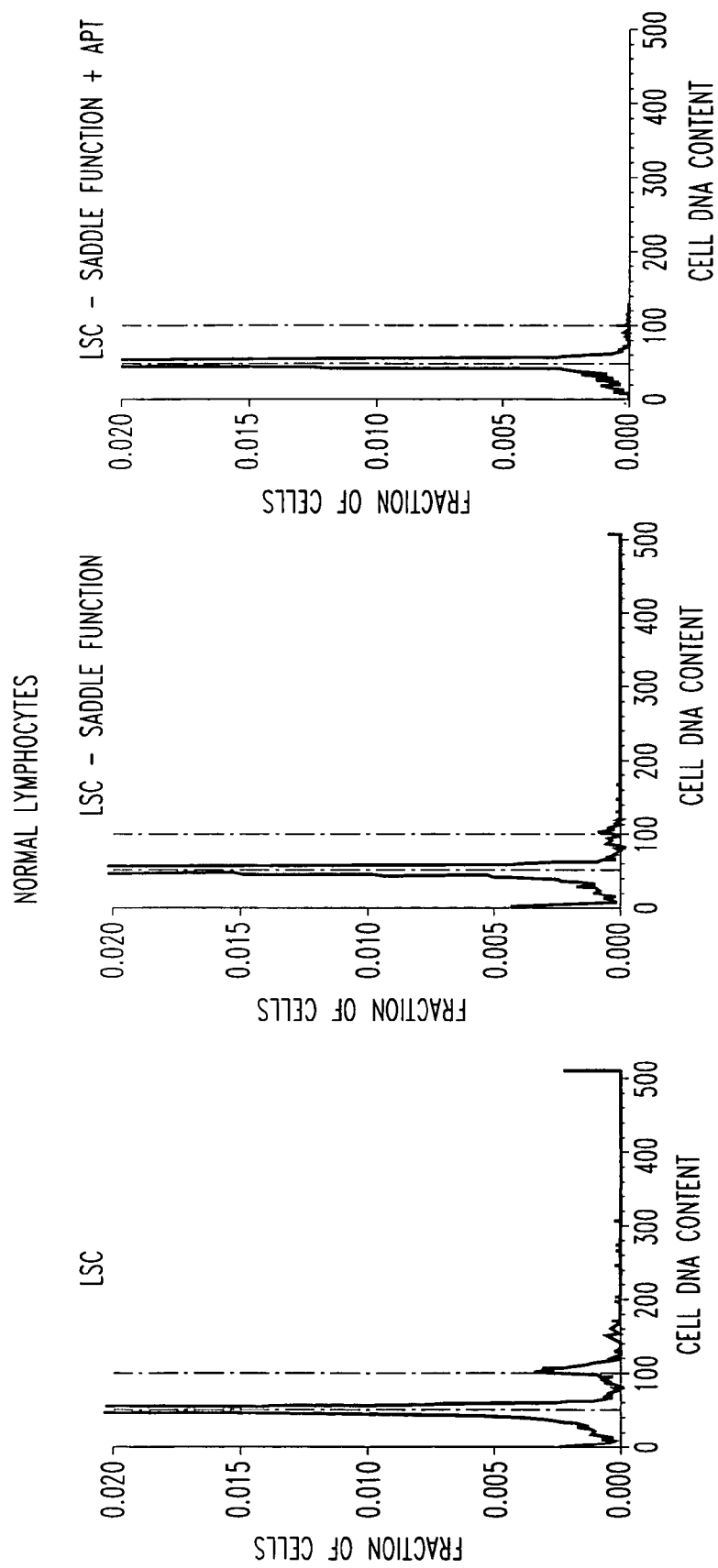

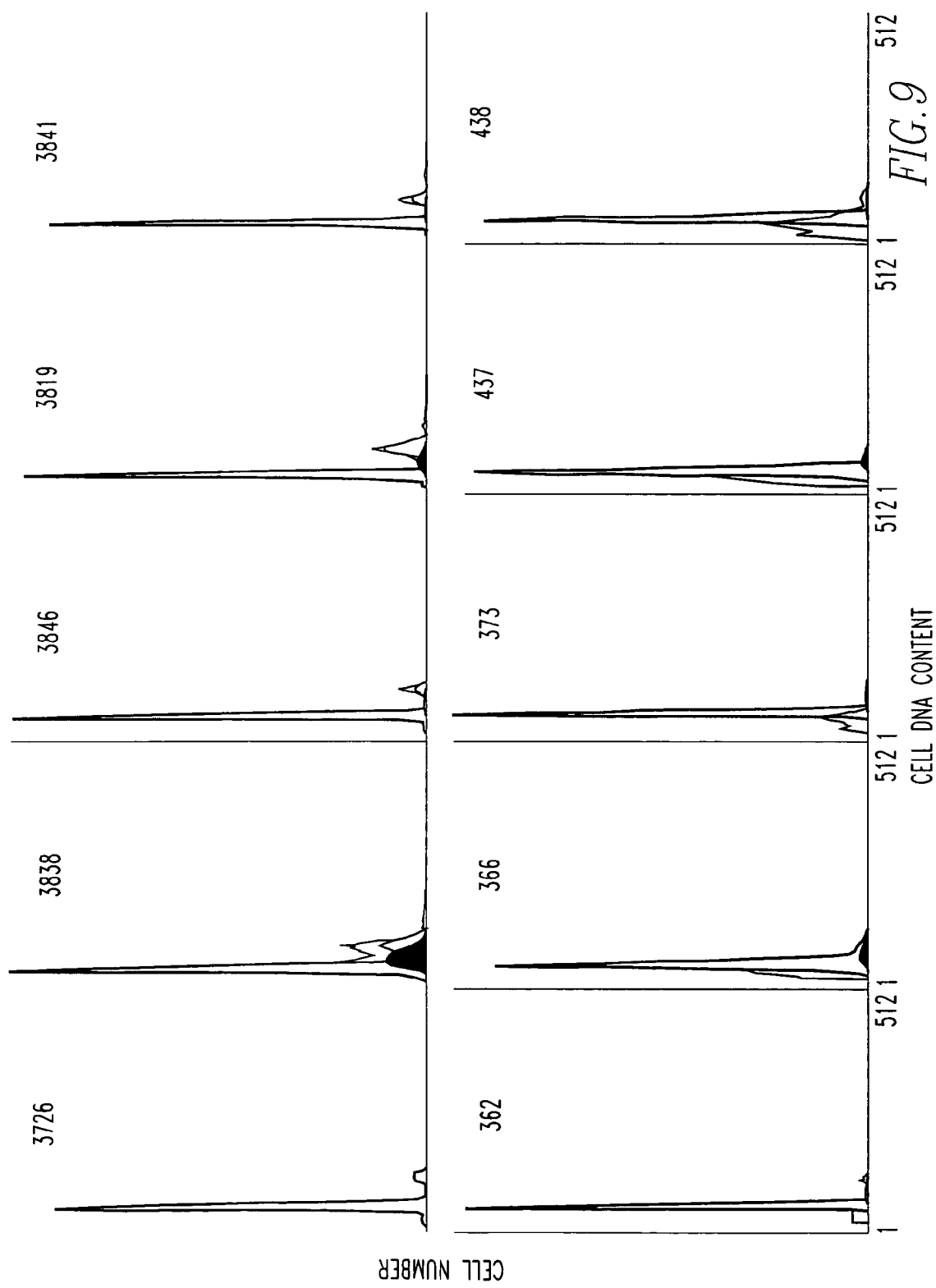

CELL AGGREGATE CORRECTION METHOD

FIELD OF THE INVENTION

The present invention is related to the identification of cell aggregates. More specifically, the present invention is related to the identification of cell aggregates with an APT function for correction of the cell aggregates in a cell suspension.

BACKGROUND OF THE INVENTION

The confounding effects of cell aggregates and cell debris on cell cycle analysis of DNA histograms obtained by flow cytometry (FCM) are well recognized (Bagwell C. Theoretical aspects of flow cytometry data analysis. In: Bauer K, Duque R, Shankey T, editors. Clinical Flow Cytometry. Baltimore: Williams and Wilkins; 1993. p. 41-61; Rabinovitch P. Practical Considerations for DNA content and cell cycle analysis. In: Bauer K, Duque R, Shankey T, editors. Clinical Flow Cytometry. Baltimore: Williams and Wilkins 117-142; 1993; Shankey TV, Rabinovitch PS, Bagwell B, Bauer KD, Duque RE, Hedley DW, et al. Guidelines for implementation of clinical DNA cytometry. International Society for Analytical Cytology. Cytometry 1993;14(5):472-7; Rabinovitch PS. DNA content histogram and cell-cycle analysis. Methods Cell Biol 1994;41:263-96; Heiden T, Castro J, Graf BM, Tribukait B. Comparison of routine flow cytometric DNA analysis of fresh tissues in two laboratories: effects of differences in preparation methods and background models of cell cycle calculation. Cytometry 1998;34(4):187-97; Wersto RP, Chrest FJ, Leary JF, Morris C, Stetler-Stevenson MA, Gabrielson E. Doublet discrimination in DNA cell-cycle analysis. Cytometry 2001;46 (5):296-306, all of which are incorporated by reference herein). Various approaches have been adopted for dealing with the problem of cell aggregates. Signal pulse shape characteristics can be used to identify cell aggregates at the time of measurement, in order to exclude them from the initial list mode data file. In practice, this approach leaves much to be desired in the analysis of disaggregated cell suspensions obtained from human solid tumors (Rabinovitch P. Practical Considerations for DNA content and cell cycle analysis. In: Bauer K, Duque R, Shankey T, editors. Clinical Flow Cytometry. Baltimore: Williams and Wilkins 117-142; 1993; Wersto RP, Chrest FJ, Leary JF, Morris C, Stetler-Stevenson MA, Gabrielson E. Doublet discrimination in DNA cell-cycle analysis. Cytometry 2001;46 (5):296-306, both of which are incorporated by reference herein). Mathematical models have been developed to deal with binned DNA histogram data to estimate the contribution of cell aggregates to various cell cycle phase regions (Bagwell C. Theoretical aspects of flow cytometry data analysis. In: Bauer K, Duque R, Shankey T, editors. Clinical Flow Cytometry. Baltimore: Williams and Wilkins; 1993. p. 41-61; Rabinovitch P. Practical Considerations for DNA content and cell cycle analysis. In: Bauer K, Duque R, Shankey T, editors. Clinical Flow Cytometry. Baltimore: Williams and Wilkins 117-142; 1993, both of which are incorporated by reference herein). However, such models do not address the effects of cell aggregation on correlated multiparameter non-DNA measurements performed on the same cells. Previously, a simple statistical approach to excluding cell aggregates from bivariate DNA/Her-2/neu data (Shackney SE, Pollice AA, Smith CA, Alston L, Singh SG, Janocko LE, et al. The Accumulation of Multiple Genetic Abnormalities in Individual Tumor Cells in Human Breast Cancers: Clinical Prognostic Implications. Cancer J Sci Am 1996;2 (2):106, incorporated by reference herein) was developed, but the method is cumbersome, and it may be of limited applicability.

Clinical multiparameter FCM studies in human breast cancer have shown that quantitative measurements of cell DNA content, Her-2/neu levels, and ras protein levels in the same cells are of clinical prognostic significance (Shackney SE, Pollice AA, Smith CA, Alston L, Singh SG, Janocko LE, et al. The Accumulation of Multiple Genetic Abnormalities in Individual Tumor Cells in Human Breast Cancers: Clinical Prognostic Implications. Cancer J Sci Am 1996;2 (2):106; Shackney S, Smith C, Pollice A, Brown K, Day R, Julian T, et al. Intracellular patterns of Her-2/neu, ras, and ploidy abnormalities in primary human breast cancers predict clinical disease free survival. In: Annual Meeting of the United States and Canadian Academy of Pathology; 2003; Washington, D.C.; 2003. p. 46A, both of which are incorporated by reference herein). Better methods were needed for development for the identification of cell aggregates in cell suspensions obtained from human solid tumors, in order to improve the ability to extract clinical prognostic information from quantitative interrelationships among multiple constituents within in each cell in such samples.

Laser scanning cytometry (LSC) is a technology that provides the opportunity to correlate multiple measurements performed on individual cells with their morphologic appearance on a cell by cell basis. The present invention involves an approach to cell aggregate discrimination that relies on features that are readily measured in each cell by LSC, in order to identify cell aggregates and exclude them from the list mode data file. This approach is validated by direct observation of ~400 individual cells in each of 21 samples of normal and malignant human cells from a variety of sources. It has been found that this approach reduces the proportions of cell aggregates in clinical samples from a mean of 20% (range, 6% to 56%) to a mean of 2.4% (range, 0-7%).

SUMMARY OF THE INVENTION

The present invention pertains to an apparatus for correcting for cell aggregates in a cell suspension from patients. The apparatus comprises a laser cytometry scanning mechanism for scanning cells of a sample of a cell suspension to obtain data about the samples patients. The apparatus comprises a memory for storing the data, the memory in communication with the scanning mechanism patients. The apparatus comprises a computer for identifying in the data cell aggregates in the samples from the samples that have been scanned with an APT function, the computer in communication with the memory.

The present invention pertains to a method for correcting for cell aggregates in a cell suspension from patients. The method comprises the steps of obtaining samples of cells from the cell suspension. There is the step of scanning by laser cytometry the samples. There is the step of storing data about the samples. There is the step of identifying in the data cell aggregates in the samples from the samples that have been scanned with an APT function.

The present invention pertains to a method for correcting for cell aggregates in a cell suspension from patients. The method comprises the steps of obtaining samples of cells from the cell suspension. There is the step of scanning the samples. There is the step of storing data about the samples. There is the step of identifying in the data cell aggregates in the samples from the samples that have been scanned with up to 98.6% accuracy.

The present invention pertains to a computer readable medium whose contents cause a computer to correct for cell aggregates in a cell suspension from patients where samples of cells from the cell suspension have been scanned by laser cytometry to obtain data about the samples which have been stored in a memory. The contents perform the steps of receiving data from the memory about the samples, and identifying in the data cell aggregates in the samples from the samples that have been scanned with an APT function.

The present invention pertains to a computer readable medium whose contents cause a computer to correct for cell aggregates in a cell suspension from patients where samples of cells from the cell suspension have been scanned by laser cytometry to obtain data about the samples which have been stored in a memory. The contents perform the steps of receiving data from the memory about the samples, and identifying in the data cell aggregates in the samples from the samples that have been scanned with up to 98.6% accuracy.

BRIEF DESCRIPTION OF THE DRAWINGS

In the accompanying drawings, the preferred embodiment of the invention and preferred methods of practicing the invention are illustrated in which:

FIGS. 1A-1H show various examples of singlets and aggregates.

FIGS. 4A-4F are histograms of fraction of cells verses cell DNA content.

FIG. 9 are histograms of cell number vs cell DNA content.

DETAILED DESCRIPTION

Figure 10:
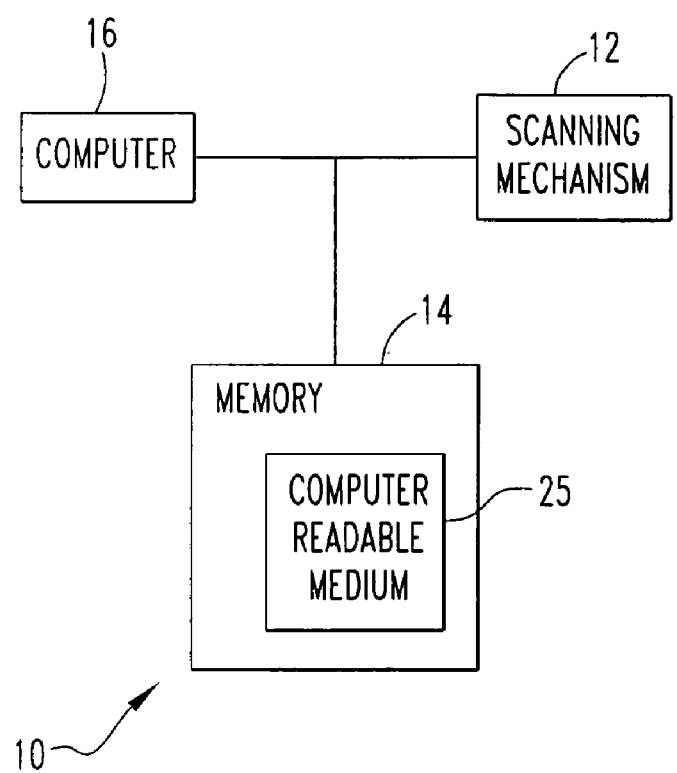
FIG. 10 is a schematic representation of an apparatus of the claimed invention.

Referring now to the drawings wherein like reference numerals refer to similar or identical parts throughout the several views, and more specifically to FIG. 10 thereof, there is shown an apparatus 10 for correcting for cell aggregates in a cell suspension from patients. The apparatus 10 comprises a laser cytometry scanning mechanism 12 for scanning cells of a sample of a cell suspension to obtain data about the samples patients. The apparatus 10 comprises a memory 14 for storing the data, the memory 14 in communication with the scanning mechanism 12 patients. The apparatus 10 comprises a computer 16 for identifying in the data cell aggregates in the samples from the samples that have been scanned with an APT function, the computer 16 in communication with the memory 14.

Preferably, the computer 16 removes cell aggregates from the data. The computer 16 preferably identifies aggregates in the data with a saddle function. Preferably, the computer 16 identifies aggregates with the APT function by forming a product from the data of the sample of a cell nuclear area and the cell perimeter normalized with respect to cell singlets from the sample. The computer 16 preferably identifies aggregates with the APT function by measuring the cell texture. Preferably, the computer 16 identifies aggregates with the APT function by measuring cell wedges in an intercellular region of a nuclear silhouette in the data of the sample.

The computer 16 preferably forms the product according to a heuristic:

$$X=\log(\text{normalized nuclear area} \times \text{normalized nuclear perimeter}),$$

where normalized nuclear area cell=cell nuclear area/mean nuclear area of G1 cells with a lowest ploidy level in the sample, and normalized nuclear perimeter=cell nuclear perimeter/mean nuclear perimeter of G1 cells with the lowest ploidy lever in the sample. Preferably, the computer 16 forms the product according to a heuristic:

$$Y=1/(\text{normalized texture value}),$$

where normalized texture value=cell texture value/mean cell texture value of G1 cells with the lowest ploidy level in the sample. The computer 16 preferably identifies aggregates by classifying cells as aggregates according to a heuristic:

$$\text{for } X<0.75, Y<0.5X,$$

and, $$\text{for } X>=0.75, \text{ all } Y.$$

The present invention pertains to a method for correcting for cell aggregates in a cell suspension from patients. The method comprises the steps of obtaining samples of cells from the cell suspension. There is the step of scanning by laser cytometry the samples. There is the step of storing data about the samples. There is the step of identifying in the data cell aggregates in the samples from the samples that have been scanned with an APT function.

Preferably, there is the step of including the step of removing cell aggregates from the data. There is preferably the step of staining cells in the samples. Preferably, the identifying step includes the step of identifying aggregates in the data with a saddle function. The identifying aggregates with an APT function preferably includes the step of forming a product from the data of the sample of a cell nuclear area and the cell perimeter normalized with respect to cell singlets from the sample.

Preferably, the identifying aggregates with an APT function includes the step of measuring the cell texture. The measuring step preferably includes the step of identifying cell wedges in an intercellular region of a nuclear silhouette in the data of the sample. Preferably, the identifying aggregates in the data with a saddle function step includes the step of identifying in the data of a sample the brightest pixel and a next brightest pixel, and determining that there are at least a plurality of pixels between the brightest pixel and the next brightest pixel.

The product forming step includes the step of forming the product according to a heuristic:

$$X=\log(\text{normalized nuclear area} \times \text{normalized nuclear perimeter}),$$

where normalized nuclear area cell=cell nuclear area/mean nuclear area of G1 cells with a lowest ploidy level in the sample, and normalized nuclear perimeter=cell nuclear perimeter/mean nuclear perimeter of G1 cells with the lowest ploidy level in the sample. Preferably, the product forming step includes the step of forming the product according to a heuristic:

$Y=1/(\text{normalized texture value})$, where normalized texture value=cell texture value/mean cell texture value of G1 cells with the lowest ploidy level in the sample. The identifying step preferably includes the step of classifying cells as aggregates according to a heuristic:

for $X<0.75$, $Y<0.5X$, and, for $X>=0.75$, all $Y$.

The present invention pertains to a method for correcting for cell aggregates in a cell suspension from patients. The method comprises the steps of obtaining samples of cells from the cell suspension. There is the step of scanning the samples. There is the step of storing data about the samples. There is the step of identifying in the data cell aggregates in the samples from the samples that have been scanned with up to 98.6% accuracy.

The present invention pertains to a computer readable medium 25 whose contents cause a computer to correct for cell aggregates in a cell suspension from patients where samples of cells from the cell suspension have been scanned by laser cytometry to obtain data about the samples which have been stored in a memory. The contents perform the steps of receiving data from the memory about the samples, and identifying in the data cell aggregates in the samples from the samples that have been scanned with an APT function.

Preferably, the medium 25 has the step of removing cell aggregates from the data. The identifying step preferably includes the step of identifying aggregates in the data with a saddle function. Preferably, the identifying aggregates with an APT function step of the medium 25 includes the step of forming a product from the data of the sample of a cell nuclear area and the cell perimeter normalized with respect to cell singlets from the sample.

The identifying aggregates with an APT function step of the medium 25 preferably includes the step of measuring the cell texture. Preferably, the measuring step of the medium 25 includes the step of identifying cell wedges in an intercellular region of a nuclear silhouette in the data of the sample. The product forming step of the medium 25 preferably includes the step of forming the product according to a heuristic:

$X=\log(\text{normalized nuclear area}\times\text{normalized nuclear perimeter})$, where normalized nuclear area cell=cell nuclear area/mean nuclear area of G1 cells with a lowest ploidy level in the sample, and normalized nuclear perimeter=cell nuclear perimeter/mean nuclear perimeter of G1 cells with the lowest ploidy level in the sample.

Preferably, the product forming step of the medium 25 includes the step of forming the product according to a heuristic:

$Y=1/(\text{normalized texture value})$, where normalized texture value=cell texture value/mean cell texture value of G1 cells with the lowest ploidy level in the sample. The identifying step preferably includes the step of classifying cells as aggregates according to a heuristic:

for $X<0.75$, $Y<0.5X$, and, for $X>=0.75$, all $Y$.

The present invention pertains to a computer readable medium 25 whose contents cause a computer to correct for cell aggregates in a cell suspension from patients where samples of cells from the cell suspension have been scanned by laser cytometry to obtain data about the samples which have been stored in a memory. The contents perform the steps of receiving data from the memory about the samples, and identifying in the data cell aggregates in the samples from the samples that have been scanned with up to 98.6% accuracy.

In the operation of the invention, the following methods and materials were used.

Cell samples. Twenty one samples of normal and malignant human cell types were studied. These included one sample of normal human lymphocytes, four samples of induced sputum obtained from normal volunteers, five human breast cancer cell lines grown in tissue culture, five disaggregated cell suspensions obtained directly from primary human breast cancers at the time of surgery, and five disaggregated cell suspensions obtained directly from primary human non-small cell lung cancers at the time of surgery. The clinical samples were all obtained with informed consent under active clinical protocols that were approved by the Institutional review board of Allegheny General Hospital, Pittsburgh, Pa. The breast cancer cell lines were SKBR-3, MB-MDA 231, MB-MDA361, MB-MDA 468, MCF-7, and JC-1939. JC-1939 cells are a breast cancer cell line that was established in the laboratory. All other cell lines were obtained from the American Type Culture Collection (Rockville, Md.). The cell lines were grown in RPMI medium, supplemented with 20% fetal bovine serum and 4% insulin-transferrin (GIBCO-BRL, Gaithersburg, Md.) at 37 degrees C. in a 5% $CO_2$ atmosphere.

Sample collection, disaggregation and fixation. Fresh lymphocytes (FLS), obtained from healthy volunteers, were separated from whole blood on a Ficoll/Hypaque density gradient, treated with 5mM DTT and fixed with 0.5% paraformaldehyde and 70% methanol, as previously described (Pollice AA, McCoy JP, Jr., Shackney SE, Smith CA, Agarwal J, Burholt DR, et al. Sequential paraformaldehyde and methanol fixation for simultaneous flow cytometric analysis of DNA, cell surface proteins, and intracellular proteins. Cytometry 1992; 13 (4):432-44, incorporated by reference herein).

Breast cancer cell lines SKBR-3, MCF-7, MDA MB 231, MDA MB 468, and JC 1939, were harvested in log phase of growth, with, trypsinaztion, edta [GIBCO-BRL] treated with cold (4° C.) 5 mM dithiothreitol (DTT) (Sigma, St. Louis, Mo.) for 15 minutes at room temperature to reduce clumping, and fixed with 0.5% paraformaldehyde followed by 70% methanol.

Freshly obtained samples from primary breast cancers and primary lung cancers were mechanically disaggregated by scissor mincing in Hanks' Balanced Salt Solution (HBSS; Mediatech, Herndon, Va.), filtered through gauze, washed with HBSS, centrifuged at 200 g for two minutes×1, treated with DTT, and fixed with 0.5% paraformaldehyde and 70% methanol. Induced sputum samples were obtained from healthy volunteers, treated with DTT, washed in HBSS and fixed with 0.5% paraformaldehyde and 70% methanol.

DNA staining. Aliquots of $2\times10^4$ fixed cells from each of the cell lines, FLS, primary tumors and sputum samples were filtered through 64 μ nylon mesh (Small Parts, Miami, Fla.), centrifuged at 200 g for two minutes×1 in PBS and resuspended in 100 ul of 4',6-diamidino-2-phenylindole (DAPI) (Sigma, St. Louis, Mo.) at a final concentration of lug/ml in v/v 1:1 Glycerol : PBS. HybriWell chambers (22×22×0.15 mm) (Schleicher & Schuell, Keene, N.H.) were affixed -to pre-cleaned glass microscope slides. 100 μl of cell suspension was pipetted through one port on the HybriWell surface while allowing the air to escape through the other port, to produce uniform cell spreading on the slide without air bubbles.

Visualization of cell aggregates. Laser Scanning Cytometry (LSC) was peformed using a Compucyte instrument (Cambridge, Mass.). A fixed scan area of $1.6 \times 10^8$ $\mu^2$ that was centered on the HybriWell chamber was used with all samples. An air-cooled, violet laser emitting at a wavelength of 405 nm was used to excite DAPI, and fluorescence was measured using a 463 nm band pass filter. Other settings included a contour mask set on the DNA measurement with a threshold of 700, 8 pixels added to threshold, an offset of 2048, and a voltage setting of 17%. The DNA index was set on the G1 peak with the lowest DNA content in the sample.

Sequential 20× microscope fields were examined visually. Each cell in the field was evaluated morphologically, and nuclear area, texture, perimeter and integrated fluorescence were recorded individually for each cell. A digital image of each field was saved. PaintShop Pro (JASC Inc., Minnetonka, Minn.) was used to number the individual cells in each field for identification and data correlation. The result of the Compucyte saddle function for each cell was also recorded. All cells in each field were included in the analysis.

Cells were classified visually as aggregates if at least two nuclei were present within the contour, and if indentation was present in the contour in the internuclear region. The classification of each cell as a singlet or aggregate was based on consensus by two experienced observers. Examples of cell singlets and aggregates of various types are shown in FIGS. 1A-1J.

The identification and removal of cell aggregates from LSC list mode data files; the saddle function. The WinCyte program provided with the CompuCyte laser scanning cytometer includes a method for identifying and removing cell aggregates that examines a contoured area that lies between the most highly fluorescent pixel within a cell (Max Pixel) and the next most highly fluorescent pixel (CompuCyte manual, 2002). If the relative fluorescence intensity of pixels within that contoured area falls below some specified value, the cell is classified as an aggregate. The value recommended by CompuCyte of 8.6% is optimal in the samples (data not shown). Herein, the CompuCyte method for identifying cell aggregates is referred to as the saddle function. FIGS. 1a-1j shows examples of the morphologic features of cell singlets and cell aggregates that determine the success or failure of this approach.

The identification and removal of cell aggregates from LSC list mode data files; the APT algorithm. A new method technique here is based on the premises that a) the combined nuclear areas of cell aggregates are likely to be substantially larger than those of G1 cells in the same cell population, b) that the perimeters of nuclear contours of cell aggregates are likely to be greater than those of round cell singlets of comparable nuclear area or cell DNA content in the same population, and c) that the products of nuclear area and nuclear contour perimeter of cell aggregates would be likely to exceed those of most cell singlets.

These are combined in the following heuristic, $X$=log(normalized nuclear area×normalized nuclear perimeter), where normalized nuclear area cell=cell nuclear area/mean nuclear area of G1 cells with the lowest ploidy level in the sample, and normalized nuclear perimeter=cell nuclear perimeter/mean nuclear perimeter of G1 cells with the lowest ploidy level in the sample.

In addition, it was apparent that the texture parameter provided by the CompuCyte instrument yielded much higher values in the cytoplasmic region of the cell than in the DAPI-stained nuclear region. At the contour threshold settings used, the contours of cell aggregates almost invariably include cytoplasmic components within the internuclear regions of cell aggregates, resulting in high overall texture values for cell aggregates.

These observations are combined in the heuristic, $Y$=1/(normalized texture value), where normalized texture value=cell texture value/mean cell texture value of G1 cells with the lowest ploidy level in the sample.

In normal and malignant cell populations obtained from clinical samples, a diploid G1 is almost always present that can serve as the G1 reference for normalization. In four of the five breast cancer cell lines that were tested here, the lowest G1 peaks present had DNA indices that were aneuploid relative to normal human lymphocytes.

A function was sought to discriminate cell aggregates from cell singlets, a) that was simple to apply, b) that would yield acceptable results independently of sample type, and c) that would achieve a balance between maximizing the elimination of cell aggregates that would degrade the quality of multiparameter data, and minimizing the loss of true cell singlets to subsequent analysis. In view of the intended goal of improving the quality of non-DNA measurements in multiparameter studies, between increasing cell singlet purity was favored over improving final cell yield.

Cells are classified as aggregates in accordance with the following heuristic:

for $X<0.75$, $Y<0.5X$, and, for $X>=0.75$, all $Y$.

Statistical analysis. Differences in the means of continuous variables were evaluated by the student t test. Cell cycle analysis was performed using the MultiCycle program (Phoenix systems), using the partial slicing debris correction, and the random aggregation with least squares convergence correction.

General cell sample characteristics. Table 1 summarizes basic features of a variety of disaggregated cell suspensions from 21 normal and malignant human epithelial cell samples in which ~400 individual cells in each sample were studied and observed directly. The proportions of visually confirmed cell aggregates varied over a broad range in different samples (table 1, column D). Two normal samples (including the normal lymphocytes) contained <10% cell aggregates. Twelve samples contained less than 20% cell aggregates, and 18 of the 21 samples contained less than 30% aggregates. One sample, a disaggregated suspension of non-small cell lung cancer cells, contained 30.2% cell aggregates. Two samples contained more than 50% cell aggregates, one a cell suspension obtained from a breast cancer cell line that, and the other a disaggregated suspension of cells obtained from a primary non-small cell lung cancer.

Figure 2:
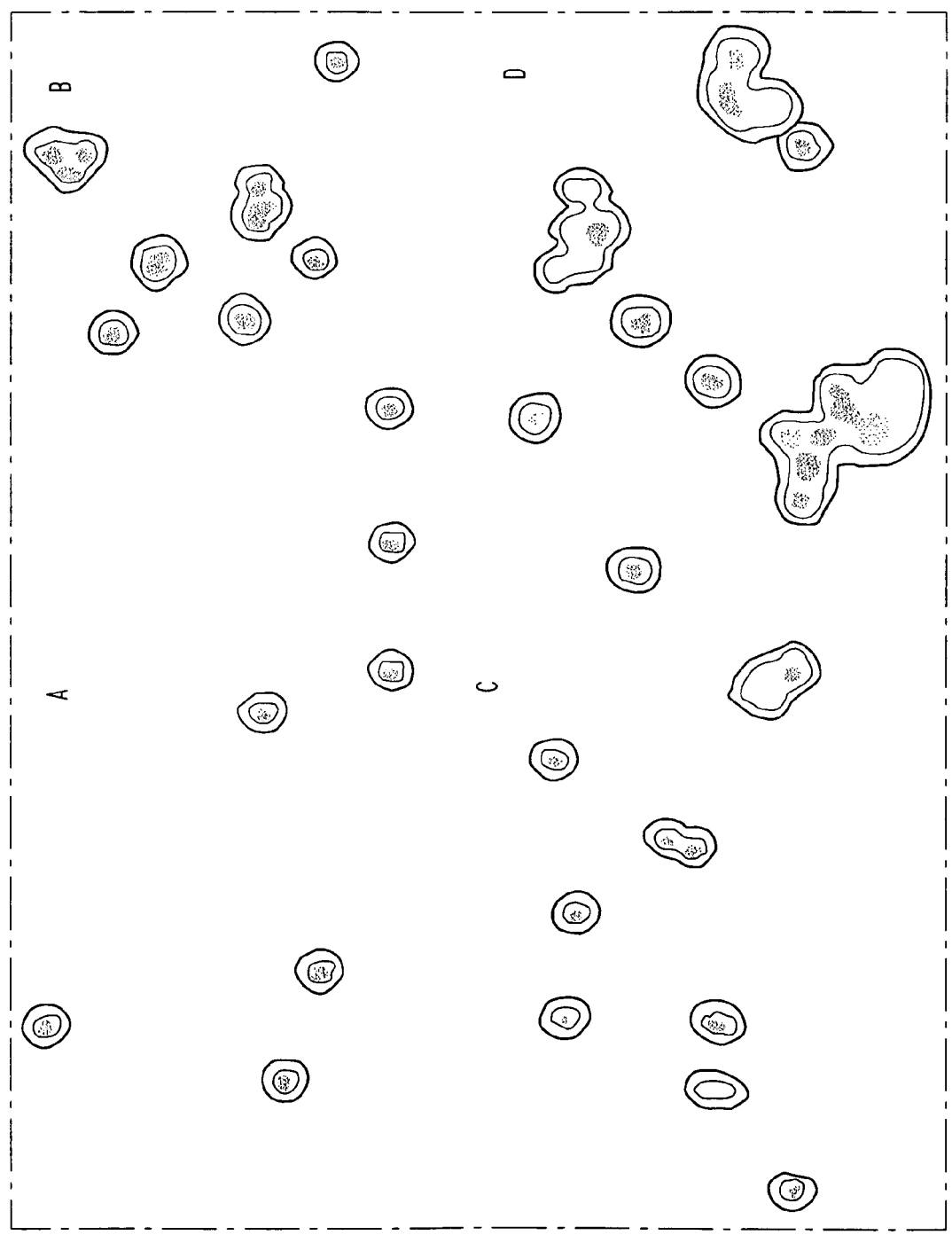
FIG. 2 shows different proportions of cell aggregates.

The cell suspensions had been dispersed on slides for LSC analysis at low cell density, to reduce the likelihood that true singlets would overlap one another by chance, and maximize the likelihood that the cell aggregates that were encountered would be composed of truly adherent cells. Representative fields from samples with different proportions of cell aggregates are shown in FIG. 2, demonstrating that at a cell density of 25,000 cells/cm² cell singlets were well dispersed, even in clumpy cell suspensions.

Visually confirmed cell singlets with cell DNA contents that exceeded the mean of the lowest G1 peak by a factor of 2.2 or more (post-$G_2M$ cells; table 1, column E) were very rarely observed in normal lymphocytes and normal sputum samples, but represented 0.7-13.5% of all cells in the tumor samples. In three of ten of the clinical samples the post $G_2M$ true cell singlet fraction exceeded 5%, and these cells are associated with prominent aneuploid populations in two of these. Cell singlets with cell DNA contents that exceeded the mean of the lowest $G_1$ peak by a factor of 3.8 or more (octaploid+cells; table 1, column F) were not observed in normal lymphocytes and normal sputum samples, and were rare in the tumor samples reaching 2% in only 1 case. These cells were scattered throughout the octaploid/hyperoctaploid region of the DNA histogram, with no evidence of clustering that might suggest a discrete $G_1$ peak in any of the samples.

Figure 3B:
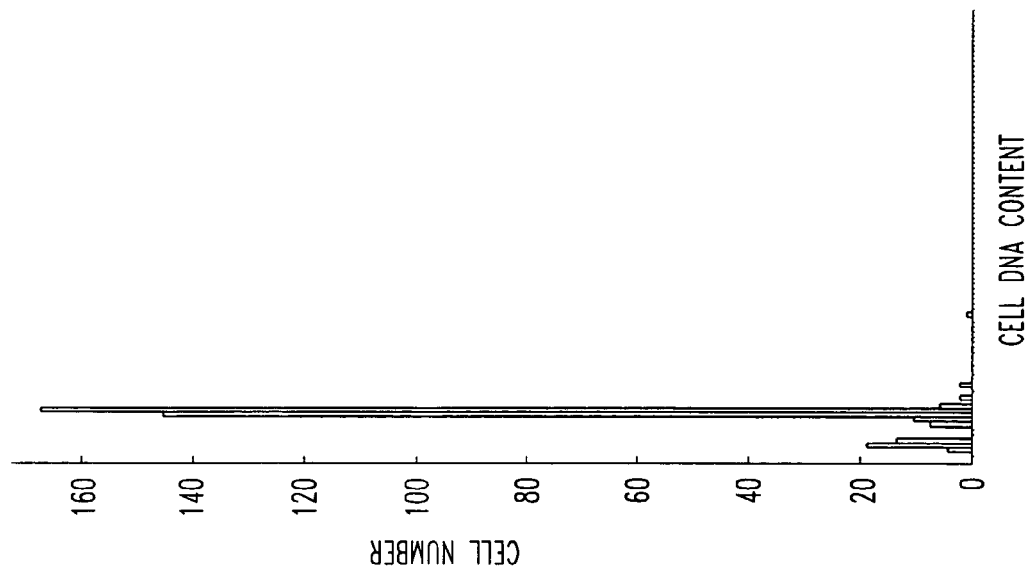
FIG. 3A and FIG. 3B show a plot of cell number versus cell DNA content.
Figure 3A:
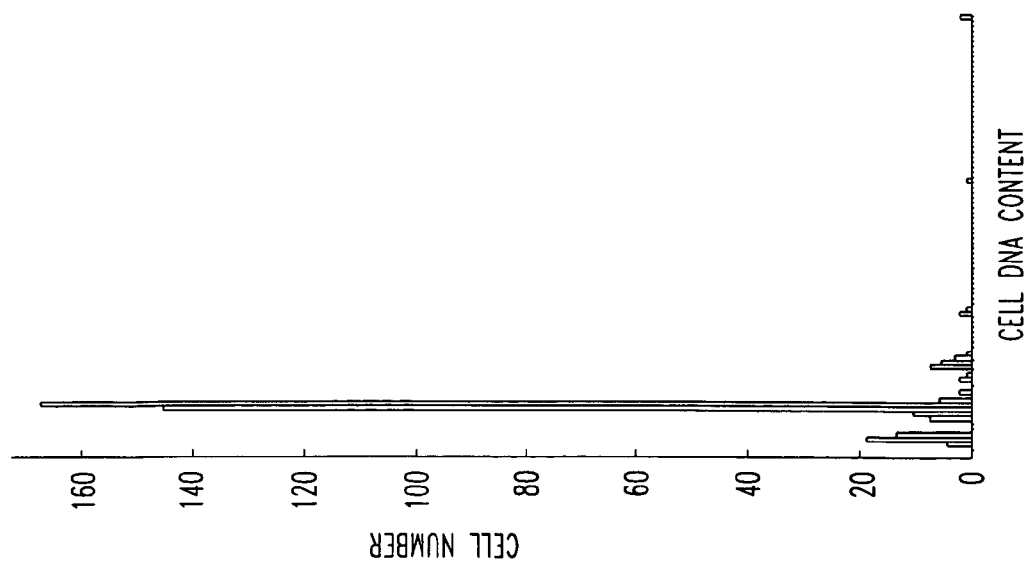

Normal human lymphocytes; a well behaved example. The performance characteristics of the combined saddle function/ APT algorithm for cell aggregate identification and removal are well illustrated in normal human lymphocytes. FIG. 3A shows a DNA histogram obtained from 401 normal human lymphocytes, each of which was examined morphologically and classified as a singlet or cell aggregate. True singlets are represented by clear bar segments, cell aggregates that were identified correctly by the saddle function are represented by gray bar segments, and cell aggregates that were identified visually but missed by the saddle function are represented by black bar segments. Nearly all of the cells included in the "$G_2M$" peak of the histogram and to the right of it are cell aggregates. This is shown more clearly in FIG. 3B. which shows the true lymphocyte cell singlets only.

Figure 3C:
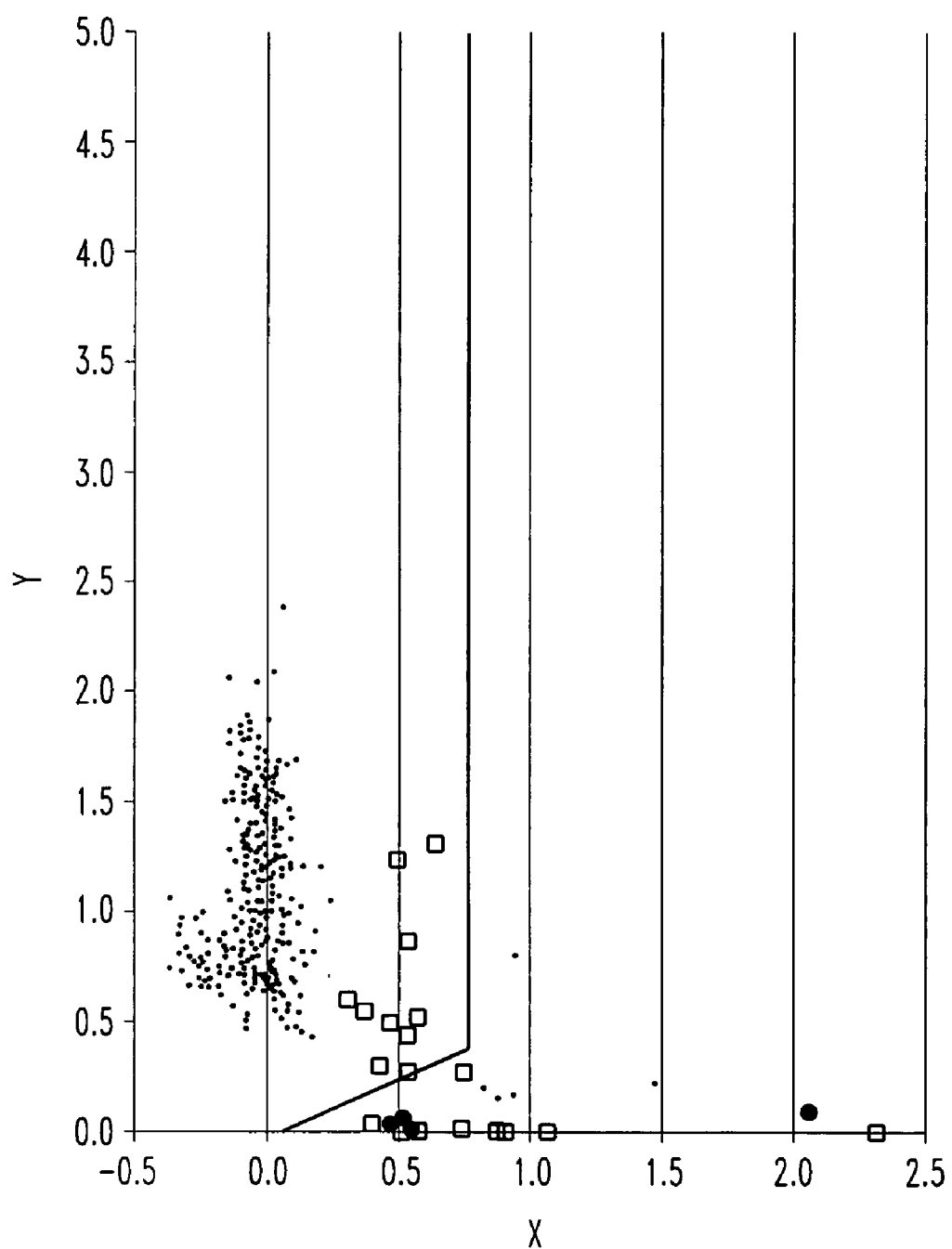
FIG. 3C shows a plot of X and Y values of individual cells obtained by the APT function.

FIG. 3C shows a plot of the X and Y values of individual cells obtained by the APT algorithm, and the discriminant lines separating putative cell aggregates from singlets. True cell aggregates that were identified by the saddle function are shown as gray squares. One of the true singlets was misclassified by the saddle function as an aggregate (false positive), and is shown as an unfilled square.

Cells that are classified as aggregates by the APT algorithm lie to the right of the discriminant lines. Nearly all of the true cell singlets, represented by small black dots, lie to the left of the discriminant lines. However, five true singlets lie to the right of the discriminant lines; these represent the cell singlets that were misclassified as aggregates by the APT algorithm (false positives).

The gray squares that lie to the left of the discriminant lines are true cell aggregates that were identified by the saddle function, but that would have been missed by the APT algorithm. The true cell aggregates that were missed by the saddle function are shown as black filled circles; all of these lie to the right of the discriminant lines. Thus, in this instance, each method identifies all of the cell aggregates that were missed by the other, resulting in a sensitivity of detection of cell aggregates for the combination of the two methods that approaches 100%. A total of only six of 377 true cell singlets were misclassified as cell aggregates by both methods. Thus, the specificity of the combined approach is 371/377, or 98.4%.

The 401 lymphocytes that were measured individually and confirmed visually as cell singlets or aggregates constituted a small subset of the >10,000 lymphocytes that were deposited on the slide in the designated 1.6 cm² scan area. The results of applying the saddle function and APT algorithm to this larger group of cells are shown FIGS. 4A-4F.

Figure 4C:
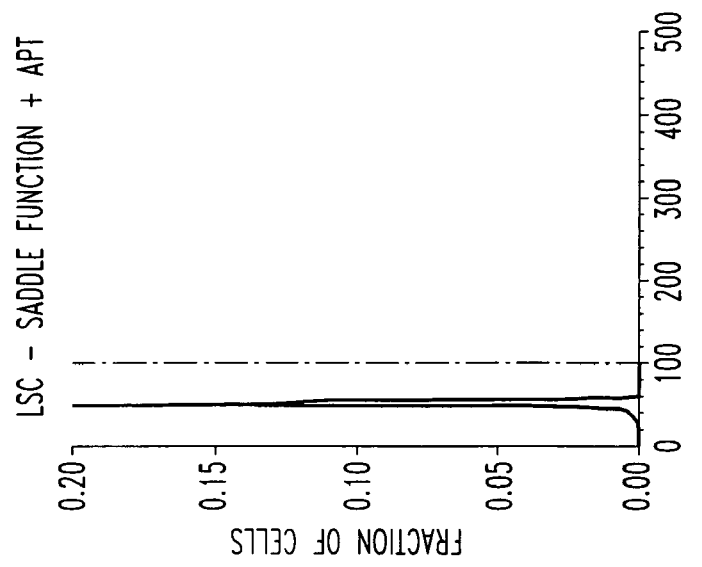
Figure 4B:
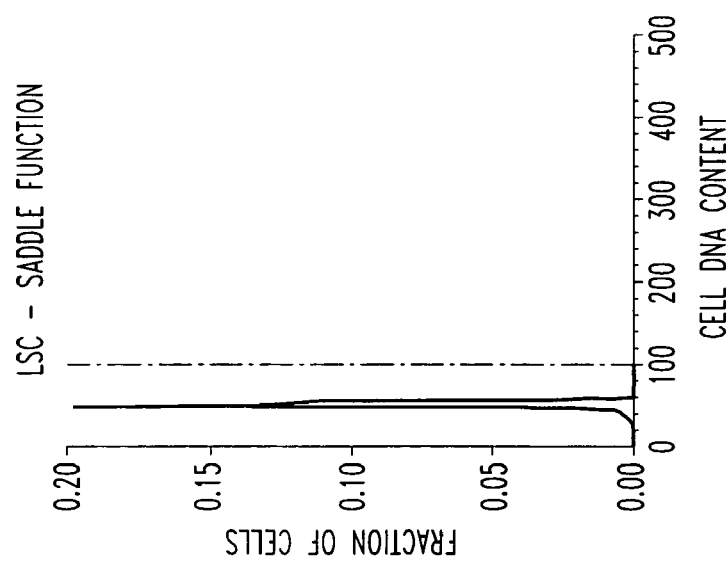
Figure 4A:
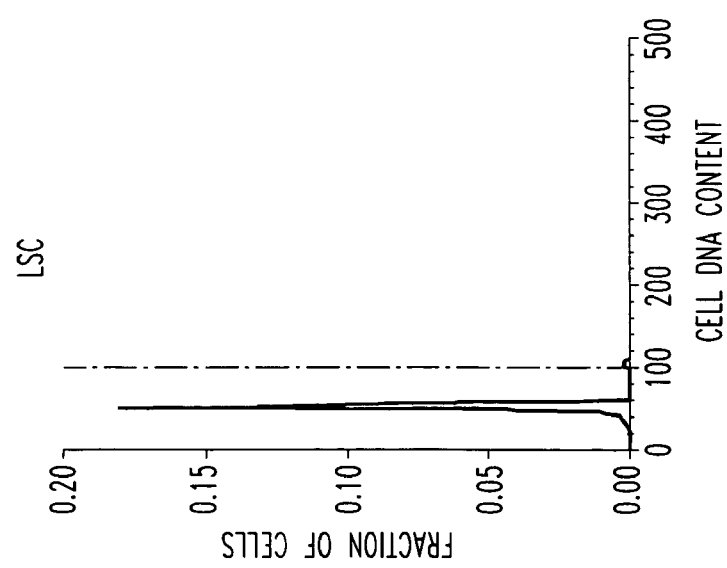

FIGS. 4A and 4B show a raw DNA histogram for DAPI-stained, paraformaldehyde/methanol-fixed, normal lymphocytes obtained by LSC, at moderate and high ordinate magnification, respectively. For purposes of comparison, all histograms are normalized with respect to total cells per sample, rather than to G1 peak height. The raw DNA histogram by LSC shows a discernable doublet peak (FIG. 4A), as well as smaller peaks that become apparent at high magnification (FIG. 4B) that are attributable to triplets and higher order aggregates. Some of these triplets and higher order aggregates were encountered as rare events in the subset of individual cells that were observed visually (FIG. 3A). It is also noted that the proportion of events due to cell debris that involves the left shoulder of the G1 peak and extends to the left of it, is larger in the LSC data than in the FCM data, due to our conservatively low threshold for excluding cell fragments based on nuclear mask area (50 square microns).

It is apparent from FIGS. 4C and 4D that most of the cells in the $G_2M$ region are now excluded from the list mode file, as are all but a few of the higher order aggregates after application of the saddle function to the list mode data file and exclusion of the cell aggregates identified by this technique. The region to the left of the G1 peak is largely unaffected. Application of both the saddle function and the APT algorithm to the data (FIGS. 4E and 4F), results in further substantial reduction of the fraction of cells with $G_2M$ DNA contents, and elimination of higher order aggregates from the list mode data file. After the application of both the saddle function and the APT algorithm, the residual proportion of cells in the sample with DNA indices greater than 1.5 is only 0.4%.

While the results in normal human lymphocytes are better than those obtained in most of the epithelial cell samples studied, they illustrate the salient performance characteristics of the saddle function and APT algorithm in a biologically unambiguous sample that contains only diploid, nonproliferating cells. The same general performance characteristics are found to carry over into more complex human epithelial tumor cell samples that contain varying proportions of cell aggregates, as described below.

Performance characteristics of the saddle function and the APT algorithm. The salient performance characteristics of the saddle function and APT algorithm separately are summarized in tables 2 and 3, respectively, and the performance characteristics of the combined approach are summarized in table 4.

The sensitivity of detection of cell aggregates (i.e., the fraction of true aggregates that was identified appropriately) in different samples ranged from 52 to 86% (mean, 72%) (table 2, column G). For the APT algorithm alone sensitivity ranged from 58% to 94% (mean, 74%) (table 3, column G). As in normal lymphocytes, when the two methods were combined, each method detected a majority of the cell aggregates that were missed by the other, resulting in increased overall sensitivities for the combined approach that ranged from 78 to 100% with a mean of 92% (table 4, column G).

Test specificity in this setting (i.e., true cell singlets/(true cell singlets+false positive cell aggregates)) can be viewed as the proportion of true cell singlets that is preserved for subsequent analysis after the exclusion of cell aggregates, taking into account those cell singlets that were wrongly excluded. Specificity decreases as the proportion of true cell singlets that are misidentified as aggregates increases. Specificity for cell singlet detection ranged from 94 to 100% (mean, 97%) for the saddle function (table 2, column H) and 89 to >99% (mean, 97%) for the APT algorithm (table 3, column H). The specificities for aggregate detection for the combined approach ranged from 86-99% with a mean of 95% (table 4, column H).

In this setting, test negative predictive value (PV−) is the fraction of all cell singlets that was appropriately identified as true singlets (i.e., true singlets/(true singlets+false negative cell aggregates), that is, PV− is a measure of the level of confidence that the cells that are preserved for analysis after the exclusion of cell aggregates are truly cell singlets. The singlet predictive value for the combined approach ranged from 92.7 to 100%, with a mean of 97.6% (table 4, column I). Conversely, the fraction of residual cell aggregates that remained in the sample after aggregate exclusion ranged from 0 to 7.3%, with a mean 2.4%. This compares with aggregate fractions ranging from 6% to 56% (mean 20%; from table 1) prior to aggregate correction.

Specific examples are now provided that demonstrate the results of the combined approach in several human epithelial primary tumor samples, graphically illustrating how these results relate to test sensitivity, specificity, and singlet predictive value (PV−).

Figure 5A:
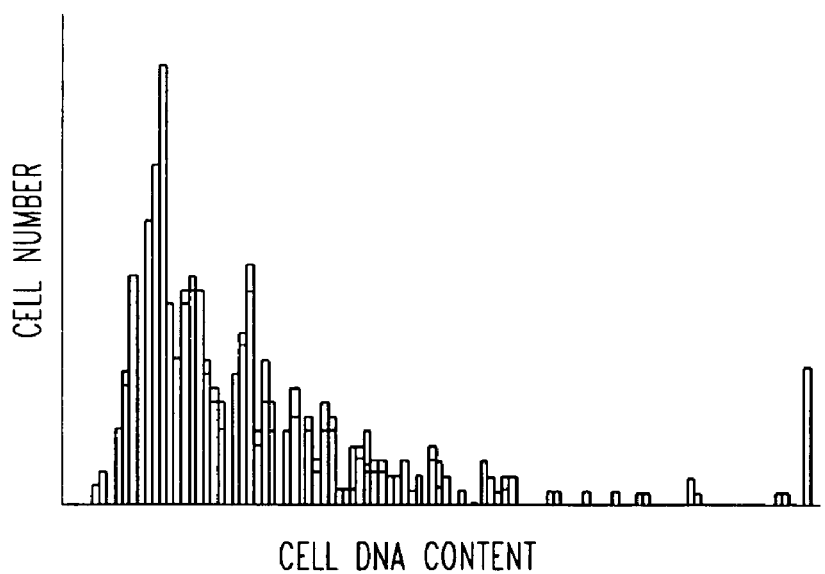
FIGS. 5A and 5B are histograms of cell number verses cell DNA content.
Figure 5B:
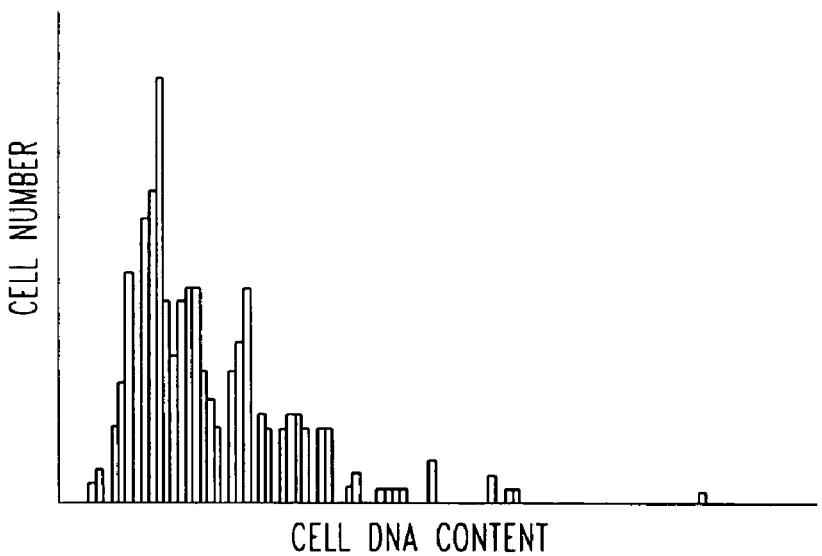

Sample 3655. Sample 3655 is a disaggregated cell suspension of cells obtained from a primary human breast cancer. The DNA histogram obtained from 400 cells that were visualized and measured individually is shown in FIG. 5A. The histogram appears to be complex, but distinct aneuploid peaks are difficult to discern in this small aliquot of cells. As indicated in table 1, there are 87 visually confirmed cell aggregates (22%) in this sample. These begin to show up in increasing numbers in the tetraploid region of the histogram, and comprise the vast majority of the cells in the octaploid and hyperoctaploid region. Of interest, some cell aggregates have near-diploid cell DNA contents. On inspection, these cells appeared to be paired cell fragments. A histogram showing only the visually confirmed cell singlets is shown in FIG. 5B. It is apparent that cell singlets are rare in the octaploid region and beyond.

Figure 5C:
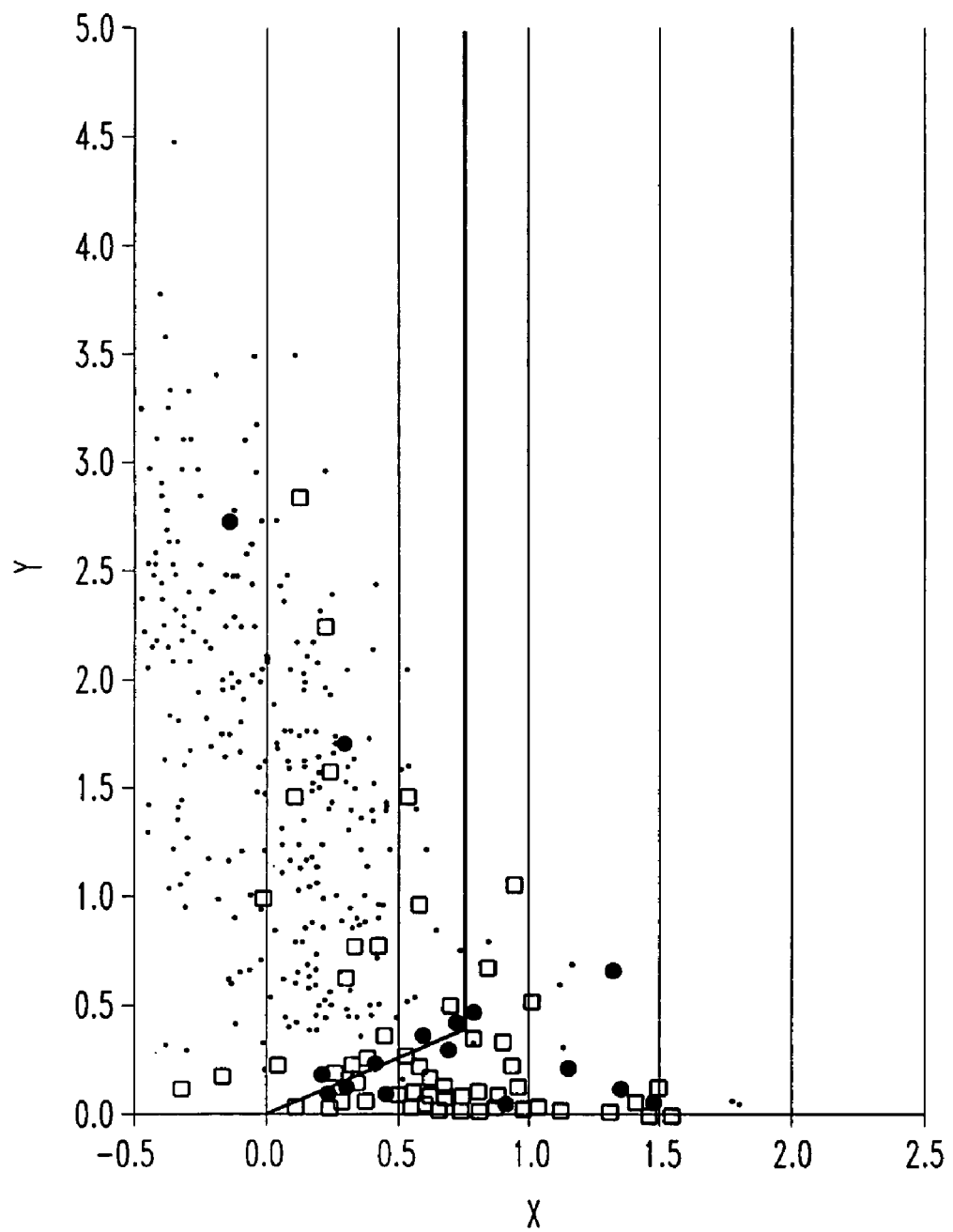
FIG. 5C is a plot of X and Y values of individual cells.

The results of applying the combined method to this cell population are shown in FIG. 5C. The gray squares to the left of the discriminant lines represent the true aggregates that were properly identified by the saddle function but not by the APT algorithm. Among the true cell aggregates that were missed by the saddle function (black filled circles), 12 were identified appropriately by the APT algorithm (black filled circles to the right of the discriminant lines) and 6 were not. This accounts for the sensitivity of 95% for the combined method in this case (table 4, column G). There were 7 true singlets that were misidentified as cell aggregates by the saddle function (white squares, FIG. 7B, and table 2, column C), and 22 true cell singlets that were misidentified as cell aggregates by the APT algorithm (black dots to the right of the discriminant lines, and table 3, column C). Two of these singlets were misidentified by both techniques. Because of these false positives, the specificity which was for each method alone (table 2 and 3, column H), was only 95% for the combined method (table 4, column H).

Figures 6A, 6B, 6C:
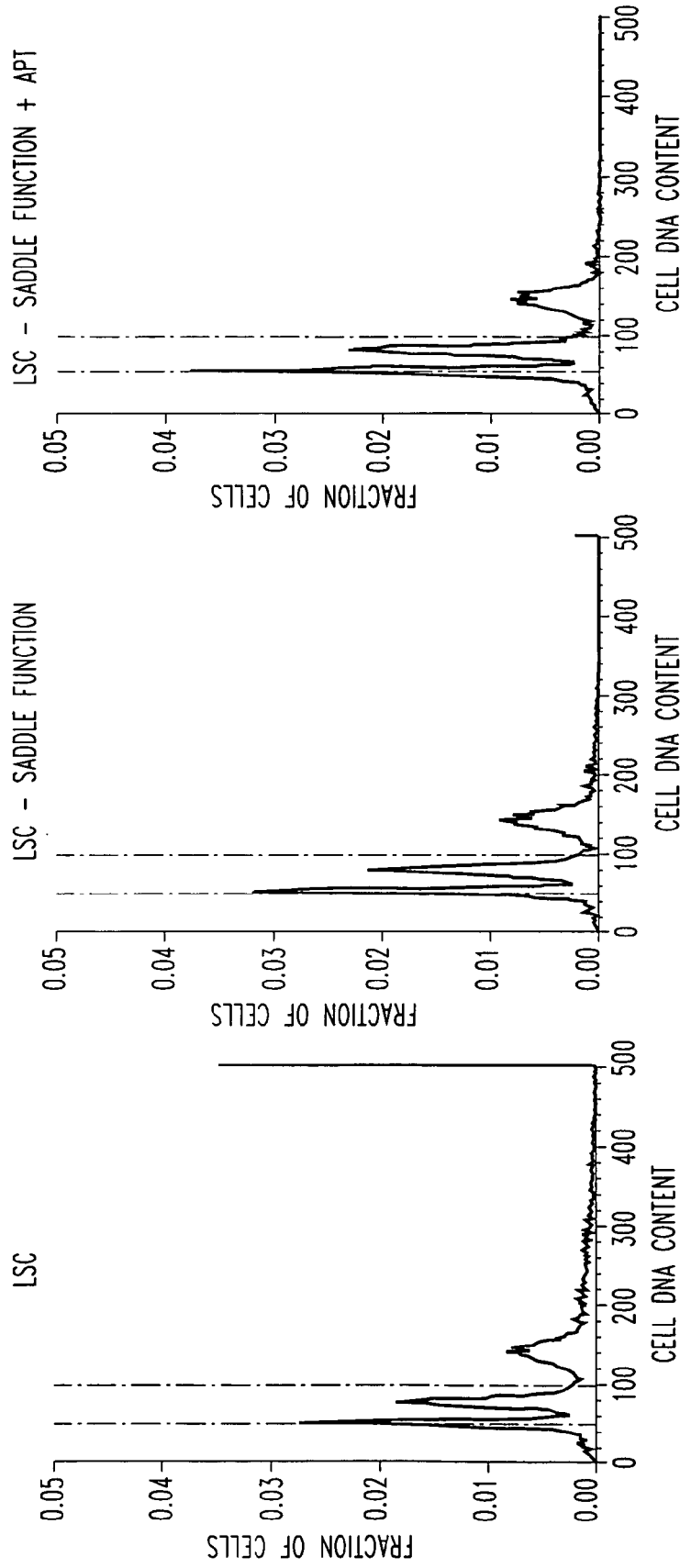
FIGS. 6A-6F are histograms of fraction of cells vs cell DNA content.
Figures 6D, 6E, 6F:
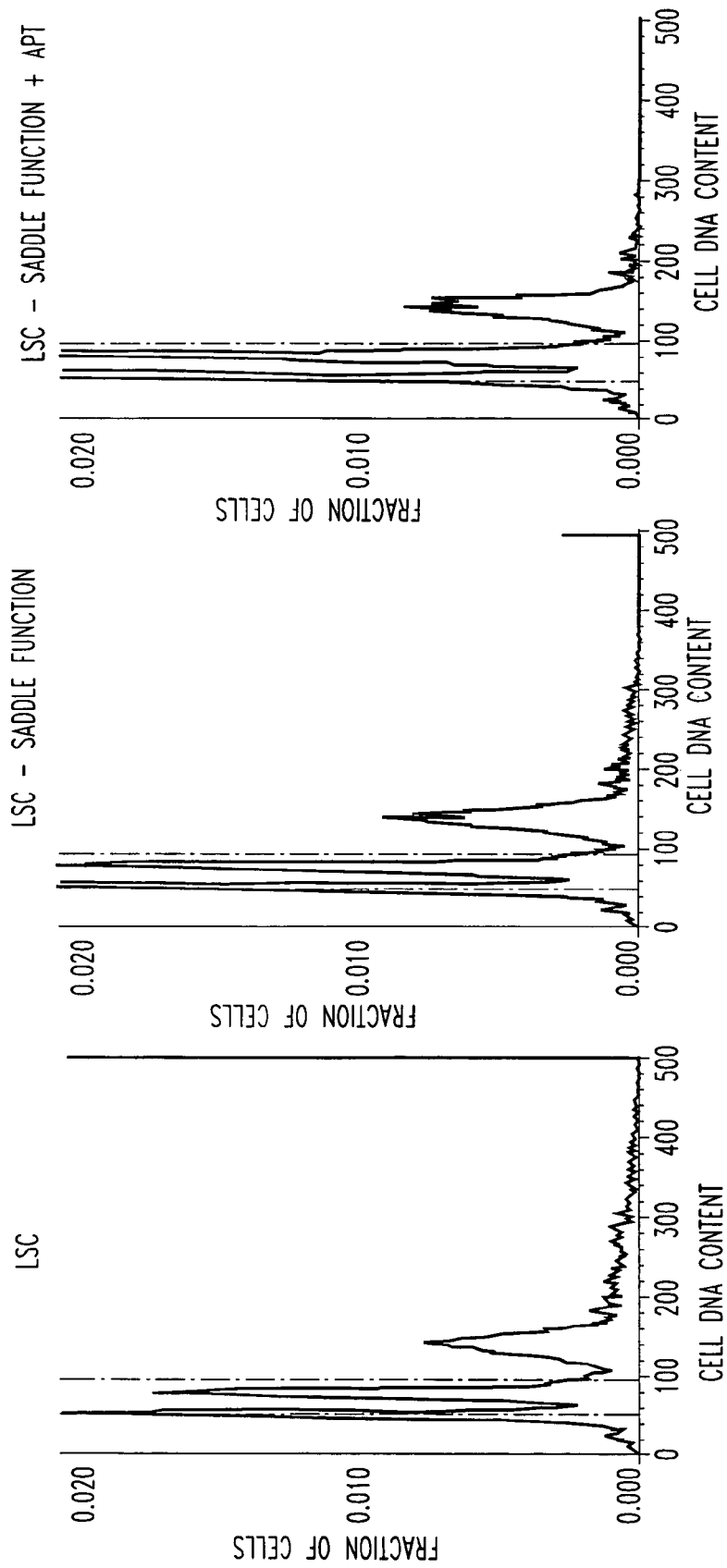

The effects of the saddle function and the APT algorithm on the DNA histogram obtained on the entire sample are shown in FIGS. 6A-6F. The raw LSC data are shown in FIG. 6A, and on a magnified ordinate scale in FIG. 6B. The left-most G1 peak in the histogram has a DNA index of 1 relative to normal human lymphocytes. The histogram also exhibits a prominent hypotetraploid G1 peak, and a smaller hypertetraploid G1 peak population the S phase region of which blends in with a gradually decreasing background that extends far beyond the octaploid region. Application of the saddle function alone (FIGS. 6C and 6D) produces a reduction in background that is discernable in the hypertetraploid region, and extends well beyond the hyperoctaploid region, while leaving the other features of the histogram largely unaltered. The combined method (FIGS. 6E and 6F) produces a further reduction in the proportion of cells in the hypertetraploid to hyperoctaploid region, with preservation of a small proportion of the cells in hypertetraploid S region. The region of the histogram spanning cell DNA contents in the octaploid and hyperoctaploid region is virtually cleared of cells. The corrected histogram is similar in most respects to the histogram of true cell singlets shown in FIG. 5A, except that the former shows better delineation of the aneuploid, and the latter shows rare true singlets in the octaploid and hyperoctaploid regions that are not preserved in FIGS. 6E and 6F.

Sample 3852. Sample 3852 is a disaggregated cell suspension of cells obtained from a primary human non-small cell lung cancer. The DNA histogram obtained by LSC from 402 cells that were examined visually and measured individually is shown in FIG. 7A. This cell subpopulation contained 130 (32%) visually confirmed cell aggregates. The left-most G1 peak in the histogram has a DNA index of 1 relative to normal human lymphocytes. There is a cell subpopulation with a prominent hypotetraploid G1 peak that is composed entirely of true cell singlets. The true singlets in the hypotetraploid S phase region of the histogram are admixed with a larger subpopulation of cell aggregates that is broadly distributed from the diploid G2M region to the hyperoctaploid region of the histogram. A histogram showing only the visually confirmed cell singlets is shown in FIG. 6B. The segment of the DNA histogram that spans the octaploid and hyperoctaploid regions includes only three cells that were classified visually as true singlets.

Figure 7B:
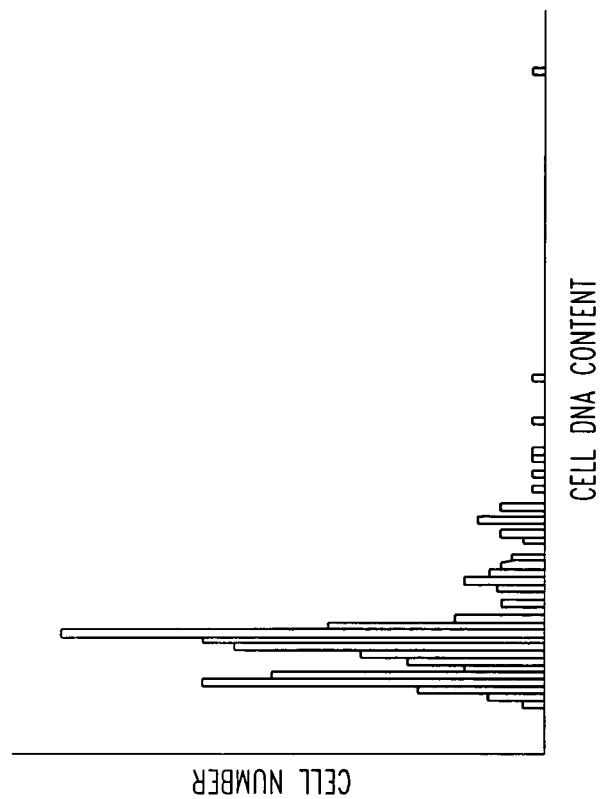
FIGS. 7A and 7B are histograms of cell number verses cell DNA content.
Figure 7A:
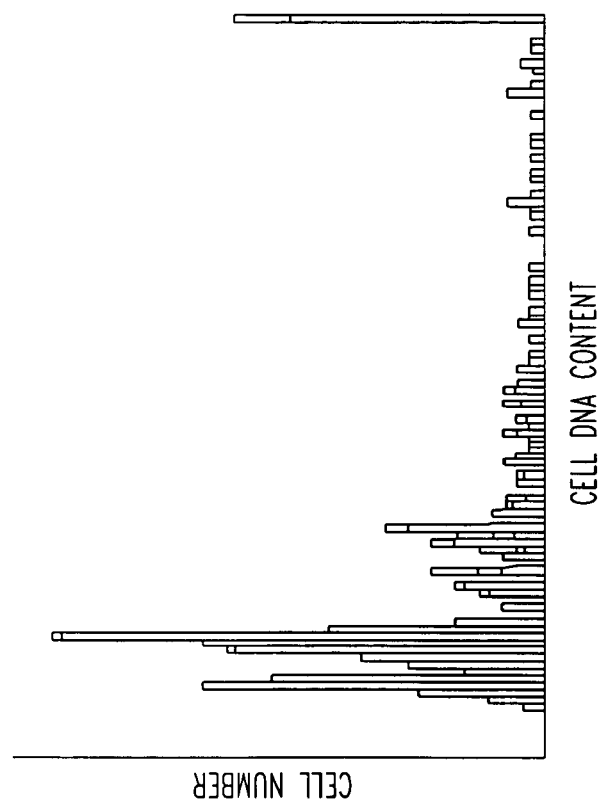

The results of applying the combined method to this cell subpopulation are shown in FIG. 7B. Among the true cell aggregates that were missed by the saddle function (black filled circles), all but one was identified appropriately by the APT algorithm (black filled circles to the right of the discriminant lines). This accounts for the sensitivity of 99% for the combined method in this case (table 4, column G). There were 7 true singlets that were misidentified as cell aggregates by the saddle function (white squares, FIG. 7B), and 55 true cell singlets that were misidentified as cell aggregates by the APT algorithm (black dots to the right of the discriminant lines). This accounted for the specificity of 78% for the combined method (table 4, column H), the lowest observed among all of the samples.

Figure 8A:
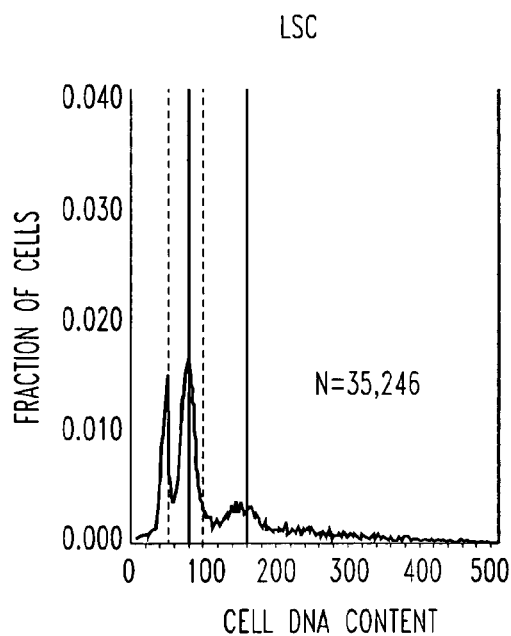
FIGS. 8A-8D are histograms of fraction of cells verses cell DNA content.
Figure 8B:
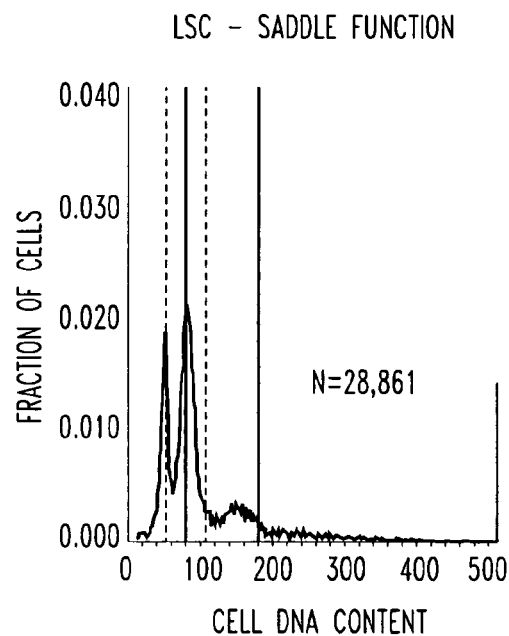
Figure 8C:
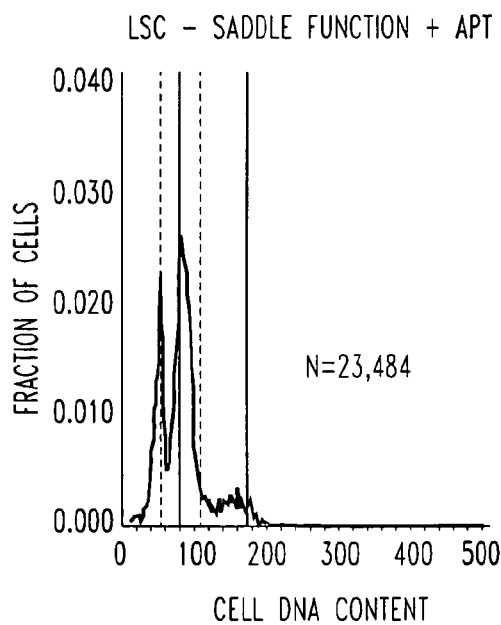
Figure 8D:
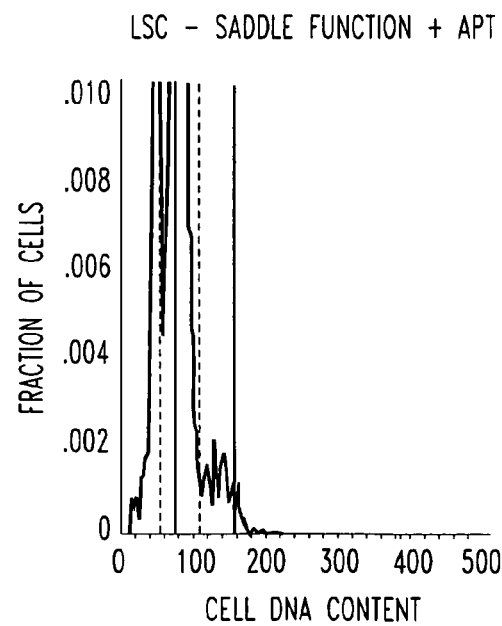

The effects of the saddle function and the APT algorithm on the DNA histogram obtained on the entire sample are shown in FIGS. 8A-8D. The uncorrected DNA histogram obtained by LSC is shown in FIG. 8A. The histogram exhibits a diploid $G_1$ peak, a prominent hypotetraploid $G_1$ peak, a lower, broader peak in the $G_2M$ region of the hypotetraploid population, and a long tail extending far beyond the octaploid region. The effects of application of the saddle function alone are shown in FIG. 8B. The hypotetraploid $G_2M$ peak remains largely unaffected, but the proportion of the cells to the right of it is reduced. The effects of the combined method are shown in FIGS. 8C and 8D. Most of the cells in hypotetraploid S region are preserved, the height of the hypotetraploid $G_2M$ peak is reduced substantially, and the region of the histogram with higher cell DNA contents is virtually cleared of cells. The corrected histogram is similar in most respects to the histogram of true cell singlets shown in FIG. 7A, with the exception that the latter shows rare true singlets in the octaploid and hyperoctaploid regions that are not preserved in FIGS. 8C and 8D.

Aggregate discrimination in relation to cell DNA content. One might anticipate that overlap in the nuclear areas and nuclear perimeters of cell singlets and cell aggregates would be most extensive among cells with DNA contents that extend from the $G_2M$ through the hyperoctaploid range. This is both because the apparent DNA contents of cell aggregates are predominantly in this range, and because singlets with DNA contents in this range are likely to have large nuclear areas and nuclear perimeters. The performance characteristics of the combined saddle function and APT algorithm in the hypertetraploid region of the DNA histogram would be of special importance in clinical samples, where the balance between cell singlet yield and cell singlet purity is critical in the analysis of aneuploid cells. Table 5 summarizes the performance characteristics of the combined saddle function and APT algorithm by DNA histogram region in the cell sub-samples that were examined visually cell by cell. Cells were grouped first by DNA content as follows: cells with DI<1.8 were assigned to the G1+S group (including hypotetraploid G1+S). Cells with DI's ranging between 1.8 and 2.2 were assigned to the "$G_2M$" group. The aneuploid/hypertetraploid group consisted of cells with DNA indices ranging from 2.2 to 3.8. Cells were classified as octaploid+ if their DNA indices exceeded 3.8. Because of the small numbers of cells in the aneuploid/hypertetraploid and octaploid+regions in individual samples, data from individual samples were pooled and averaged within each DNA content subclass, and this was done for all DNA content subclasses and this was done for all DNA content subclasses.

It is apparent from table 5 that prior to aggregate correction the singlet fraction is highest (0.97) in the G,S region of the histogram, and falls progressively from 0.53 in the $G_2M$ region to 0.35 in the hypertetraploid region (table 5, row 5). The combined use of the saddle function and APT algorithm results in a singlet fraction of 0.8 or greater in every region of the DNA histogram (table 5, row 6). However, the maintenance of high levels of cell singlet purity is achieved at the cost of decreasing cell singlet yield in cell subsets with high DNA contents. Thus, while 97% of cell singlets with $G_1S$ DNA contents are recovered for analysis, 92% of cell singlets with $G_2M$ DNA contents are recovered, and only 74% of cell singlets with hypertetraploid DNA contents are recovered for analysis.

While the maintenance of high cell singlet purity may be a priority for multiparameter analysis, one must consider how the progressive decrease in cell yield with increasing DNA content might affect other applications involving DNA histogram data, such as cell cycle analysis. An additional statistic is provided in table 5 for this purpose.

If all singlets lost from each region were exactly counterbalanced by the retention of cell aggregates that had not been removed by the saddle function and APT algorithm in that region, then the calculation of proportions of cells in each region of the DNA histogram would not be affected adversely by cell singlet loss. The expected yield ratio (table 5, line 8), adds back the effect of the presence of false negative aggregates to estimates of proportions of cells with different cell DNA contents. Thus, for example, the persistence of aggregates in the $G_2M$ region of the DNA histogram increases the overall recovery of $G_2M$ cells from 92% to 108% of the value expected had all true $G_2M$ singlets been recovered at 100% purity. The loss of cell singlets from the hypertetraploid region is a little less well buffered by the persistence of false negative aggregates, as indicated by an expected yield ratio of only 0.91 (table 5, line 8, column 7). It should be noted that the values reported are averages of pooled samples, and that in individual samples the expected yield ratio may be greater than or less than 1.0.

Cell cycle analysis. The combined approach to cell aggregate removal may be useful in cell cycle analysis. For example, the distinction between diploid $G_2M$ cells and tetraploid $G_1$ peaks has long been recognized as a potentially difficult problem (Rabinovitch PS. DNA content histogram and cell-cycle analysis. Methods Cell Biol 1994;41:263-96; Baldetorp B, Bendahl PO, Ferno M, Alanen K, Delle U, Falkmer U, et al. Reproducibility in DNA flow cytometric analysis of breast cancer: comparison of 12 laboratories' results for 67 sample homogenates. Cytometry 1995;22(2): 115-27; Bergers E, Montironi R, van Diest PJ, Prete E, Baak JP. Interlaboratory reproducibility of semiautomated cell cycle analysis of flow cytometry DNA-histograms obtained from fresh material of 1,295 breast cancer cases. Hum Pathol 1996;27(6):553-60, all of which are incorporated by reference herein). The removal of cell aggregates from the list mode file can be helpful in clarifying this distinction.

Among the ten clinical samples obtained from human solid tumors that were analyzed here, five clearly exhibited aneuploid peaks after cell aggregate removal, two of which are described in FIGS. 5-8. Four of the other five samples exhibited relatively small, but clearly identifiable, sharp $G_2M$ peaks (FIG. 9, upper panels). Furthermore, the appearance of these peaks differed both qualitatively and quantitatively from the G2M regions of the normal sputum samples (compare FIG. 9, upper panels with FIG. 9 lower panels). Ordinarily, the G2M peaks in the upper panels of FIG. 9 might be dismissed as being due to contamination by cell doublets. However, the performance characteristics of the combined saddle function and APT algorithm on the subsets of visually confirmed cells in these samples would suggest otherwise.

It is apparent from table 6 that while the fractions of cells in S phase estimated by the Multicycle model (Phoenix systems) are not substantially different in the "diploid" tumors and in the normal sputum samples (table 6, column B), the average Multicycle model estimates of the fractions of cells in $G_2M$ were greater in the "diploid" tumors by nearly 16-fold (table 6, column C). It is of interest that the overall ranges and mean estimates of the residual percentages of aggregates by the MultiCycle model are similar to the visually confirmed percentages (table 6, compare columns E and F). The average purity of visually confirmed cell singlets in the $G_2M$ region was 0.74 (range 0.58-0.95 in the aggregate-corrected tumor samples, and was 0.72 (range 0.3-1.0) in the normal sputum samples (table 6, column G), indicating that the observed $G_2M$ peaks consisted mostly of true cell singlets in most sample types. The average expected yield ratios exceeded 1 in both sample types, and was actually higher in the normal samples (1.84 vs. 1.30; table 6, column H). Based on these findings, one would conclude that the greater proportions of cells in the $G_2M$ region of the DNA histogram in the "diploid" tumors as compared with the normal sputum samples (table 6, column C) are not likely to be due to systematic differences in the proportions of cell aggregates between the two cell types.

The most telling statistic with regard to the characterization of the cells in the $G_2M$ region of the DNA histogram is the "$G_2M$"/S ratio, given in table 6, column D. This is the ratio of the proportions of cells in the G2M region to the proportion of cells in the S region within each sample. In proliferating cell populations, this proportion cannot exceed the ratio of the duration of $G_2M$ phase to the duration of S phase (Steele G. Basic theory of growing cell populations. In: Steele G, editor.

Growth Kinetics of Tumours. Oxford: Clarendon Press; 1977. p. 56-85, incorporated by reference herein). Thus, for example, assuming an average S phase duration of 12-24 hours in human tumor cells, in a clinical sample with a "$G_2M$"/S ratio of 2, either one must conclude that the average duration of $G_2M$ is at least 24-48 hours in that sample, or one must seek a more plausible alternative explanation. Indeed, it seems likely that most of the "$G_2M$" cells in the "diploid" tumors examined here are, in fact, members of tetraploid G, peaks. This raises the possibility that the presence of small tetraploid subpopulations in human solid tumors may be much more common than has been appreciated.

It has been recently shown that the disease-free survival of breast cancer patients whose tumors contained at least 5% of cells that exhibited simultaneous aneuploidy, Her-2/neu overexpression and ras overexpression was significantly worse than patients whose tumors did not meet this criterion, independently of nodal status and tumor size (Shackney S, Smith C, Pollice A, Brown K, Day R, Julian T, et al. Intracellular patterns of Her-2/neu, ras, and ploidy abnormalities in primary human breast cancers predict clinical disease free survival. In: Annual Meeting of the United States and Canadian Academy of Pathology; 2003; Washington, D.C.; 2003. p. 46A, incorporated by reference herein). In these studies, the data were collected by multiparameter flow cytometry on cells that were obtained fresh from primary tumor samples at the time of surgery, and prepared for analysis by mechanical disaggregation into whole cell suspensions prior to fixation in paraformaldehyde and methanol. These studies demonstrate that there are correlations among intracellular molecular constituents of cells that are of potential clinical relevance, which can be studied in heterogeneous human tumor cell populations by performing multiple correlated measurements on large numbers of intact whole cells.

The need for a 5% threshold in these studies may have been due, at least in part, to the presence of residual cell aggregates in the sample, despite the use of peak vs. integrated signal gating during data collection and despite attempts to correct for cell aggregates by other means (Shackney SE, Pollice AA, Smith CA, Alston L, Singh SG, Janocko LE, et al. The Accumulation of Multiple Genetic Abnormalities in Individual Tumor Cells in Human Breast Cancers: Clinical Prognostic Implications. Cancer J Sci Am 1996;2(2):106, incorporated by reference herein). The presence of substantial proportions of cell aggregates in cell suspensions obtained from human solid tumors is a well recognized problem (Rabinovitch P. Practical Considerations for DNA content and cell cycle analysis. In: Bauer K, Duque R, Shankey T, editors. Clinical Flow Cytometry. Baltimore: Williams and Wilkins 117-142; 1993, incorporated by reference herein), and the relative ineffectiveness of flow cytometric peak vs. integral or peak vs. area signal gating in removing cell aggregates from such samples is also well known (Rabinovitch P. Practical Considerations for DNA content and cell cycle analysis. In: Bauer K, Duque R, Shankey T, editors. Clinical Flow Cytometry. Baltimore: Williams and Wilkins 117-142; 1993, incorporated by reference herein).

There are several widely used computer modeling techniques to correct for the effects of cell aggregates on estimates of fractions of cells in different phases of the cell cycle from single parameter DNA histograms (Rabinovitch P. Practical Considerations for DNA content and cell cycle analysis. In: Bauer K, Duque R, Shankey T, editors. Clinical Flow Cytometry. Baltimore: Williams and Wilkins 117-142; 1993, incorporated by reference herein). These methods operate on binned DNA histogram data, and are not suitable for application to data sets that consist of multiple correlated measurements on each individual member of a cell population. A relatively simple statistically based approach to cell aggregate analysis of multiparameter FCM data (Shackney SE, Pollice AA, Smith CA, Alston L, Singh SG, Janocko LE, et al. The Accumulation of Multiple Genetic Abnormalities in Individual Tumor Cells in Human Breast Cancers: Clinical Prognostic Implications. Cancer J Sci Am 1996;2(2) :106, incorporated by reference herein) has been presented. However, this approach is cumbersome to use, and its performance characteristics and general applicability are untested.

As with flow cytometry, one can perform multiple correlated cell by cell measurements on large numbers of intact cells by laser scanning cytometry. Using laser scanning cytometry one can also examine the morphology of individual cells under study, and correlate these visual observations with quantitative measurements performed on the same cells. In the present invention, this capability has been made use of to evaluate, separately and in combination, the performance characteristics of a method for the identification of cell aggregates that is provided with the CompuCyte LSC instrument (the saddle function), and the performance characteristics of an independent method that has been developed and described herein for the same purpose (the APT algorithm).

The saddle function relies on the expectation that in cell aggregates the brightest pixel and the next brightest pixel might be separated by pixels that are less bright, presumably because they lie in separate members of the aggregate (CompuCyte manual). The APT algorithm relies on a) the expectation that the product of cell nuclear area and nuclear perimeter, normalized with respect to G1 cell singlets in the same sample, would be larger for cell aggregates than for cell singlets, and, b) the observation that the nuclear silhouette of cell aggregates often includes small cytoplamic wedges in the internuclear region that have much higher texture values than the true nuclear region itself.

The average sensitivity (fraction of true aggregates detected) for the saddle function was 72% among the 21 samples that were studied here (table 2). The average sensitivity for the APT algorithm was 74% (table 3). Most of the cell aggregates missed by one method were detected by the other, so that the sensitivity of the two methods in combination increased to an average of 92% over all samples studied (table 4).

The average false positive rates (cell singlets that were misidentified as cell aggregates), were 2% for the saddle function, 2% for the APT algorithm, and 4% for the combined method (see tables 2,3,and 4). There was considerable variability from sample to sample by both methods. Vagaries in the distribution of nuclear staining intensity in cell singlets might account for false positives generated by the saddle function.

Among the false positives generated by the APT algorithm, most were due to overlapping singlet and aggregate values along the discriminant border between the two. The classification of these cells could be altered by adjustment of the discriminant function (see below). However, in some samples, there are small proportions of cells that are classified visually as singlets, but that have APT values that are well outside the singlet range.

Of note, some cells with $G_1$ or S DNA contents are identified as cell aggregates. These can arise as the result of misidentification of cell singlets as aggregates by either method. Those generated by the APT algorithm are commonly due to the aggregation of nuclear fragments with each other or with cell singlets.

The test negative predictive value, or cell singlet predictive value, is the fraction of true cell singlets in the cell sample that remains after exclusion of all of the cells that were identified as cell aggregates (the latter including both true and false positive cell aggregates). These remaining cells consist of both true cell singlets and the cell aggregates that were misidentified as cell singlets. Since the saddle function and the APT algorithm each identify most of the true cell aggregates that were missed by the other, the fraction of aggregates that are misidentified as cell singlets that remains after applying both methods is small in most, samples (average false negative rate, 1.7%; table 4). As a result, the singlet predictive value is high in most cell samples (average, >97.6%; table 4). That is, after the removal of cell aggregates by both the saddle function and the APT algorithm, on the average, more than 97.6% of the remaining cells are true cell singlets.

Despite the limited numbers of aneuploid cells available for analysis in each sample, direct visual observation of the morphological appearance of these cells has provided useful insights. First, it has been confirmed the early findings of others that cell suspensions from human solid tumors often contain proportions of cell aggregates that are in excess of 10% (Shackney SE, Pollice AA, Smith CA, Alston L, Singh SG, Janocko LE, et al. The Accumulation of Multiple Genetic Abnormalities in Individual Tumor Cells in Human Breast Cancers: Clinical Prognostic Implications. Cancer J Sci Am 1996;2(2):106, incorporated by reference herein), and it has been shown that most of these cell aggregates do, indeed have cell DNA contents that are in the $G_2M$ range and higher (tables 1 and 5). Second, it is shown that in uncorrected samples the proportions of true cell singlets that lie beyond the diploid $G_2M$ region are relatively small (<30% in most cases), even when aneuploid cell populations are present. It is also shown that nearly all of the cells in the octaploid regions of the DNA histogram and beyond are cell aggregates in most of the samples studied. However, samples with prominent hypertetraploid components often exhibit small proportions of true singlets in the octaploid region as well (see table 1, columns E and H) When the performance characteristics of the combined saddle function and APT algorithm are examined in relation to cell DNA content, it is apparent that singlet purity is maintained over a broad range of cell DNA contents. Thus, one might anticipate that application of the aggregate correction to clinical samples of human solid tumors would improve the quality of information gathered by multiparameter analysis of these cells, and particularly, of cells in the post-$G_2M$ region.

The APT algorithm depends on the measurement of cell texture, nuclear area, and nuclear perimeter on each cell. Since the ranges of values for each of these measurements differs from sample to sample, each cell-based measurement was normalized with respect to its mean value in the cells included under the G1 peak with the lowest DNA content in the same sample. The similarities in performance characteristics of the combined method for cell aggregate identification (see table 4) in 21 samples from different sources (cultured cells, sputum samples, primary solid tumors), of different types (normal or malignant, breast cancer or lung cancer), with different biological characteristics (diploid or aneuploid) and with different morphological features (cell/nuclear size), suggests that this approach may be widely applicable, particularly in the study of human solid tumors.

A Summary of the Figures is as Follows

FIG. 1 shows examples of the morphological appearance of truth singlets (A and B), true aggregates identified by the saddle function (C-E) . False negative aggregates by the saddle function can have overlapping nuclei, producing a central dark region (F), or can consist of cells with nuclei that exhibit disparate staining intensities (G) False positive aggregates by the saddle function may exhibit a course nuclear texture (H).

FIG. 2 shows singlets are well dispersed in samples containing different portions of cell aggregates. A (subnormal lymphocytes, B (J C-1939 cells, C) tumor sample 3849, D)tumor sample 3852.

FIG. 3 shows normal lymphocytes. 3A (DNA histogram of visually confirmed singlets and aggregates. Gray regions represent aggregates that were detected by the cell function. Black regions represent cell aggregates that were missed by the cell function. 3B) is a DNA histogram of visually confirmed singlets only. 3C (a plot of the X and Y components of the APT algorithm for individual visually confirmed cells.

FIG. 4. 4A) DNA histogram of the entire sample, uncorrected, 4B) same as 4A, but at higher ordinate magnification. 4C) DNA histogram of the entire sample, corrected for aggregates with saddle function only, 4D) same as 4C, but at higher ordinate magnification. 4E) DNA histogram of entire sample, corrected for aggregates with saddle function plus APT algorithm, 4F) same as 4E, but at higher ordinate magnification.

FIG. 5. Tumor sample 3655. 5A, 5B, and 5C, as in FIG. 3.

FIG. 6. Tumor sample 3655. 6A, 6B, 6C, 6D, 6E, 6F, as in FIG. 4.

Figure 7C:
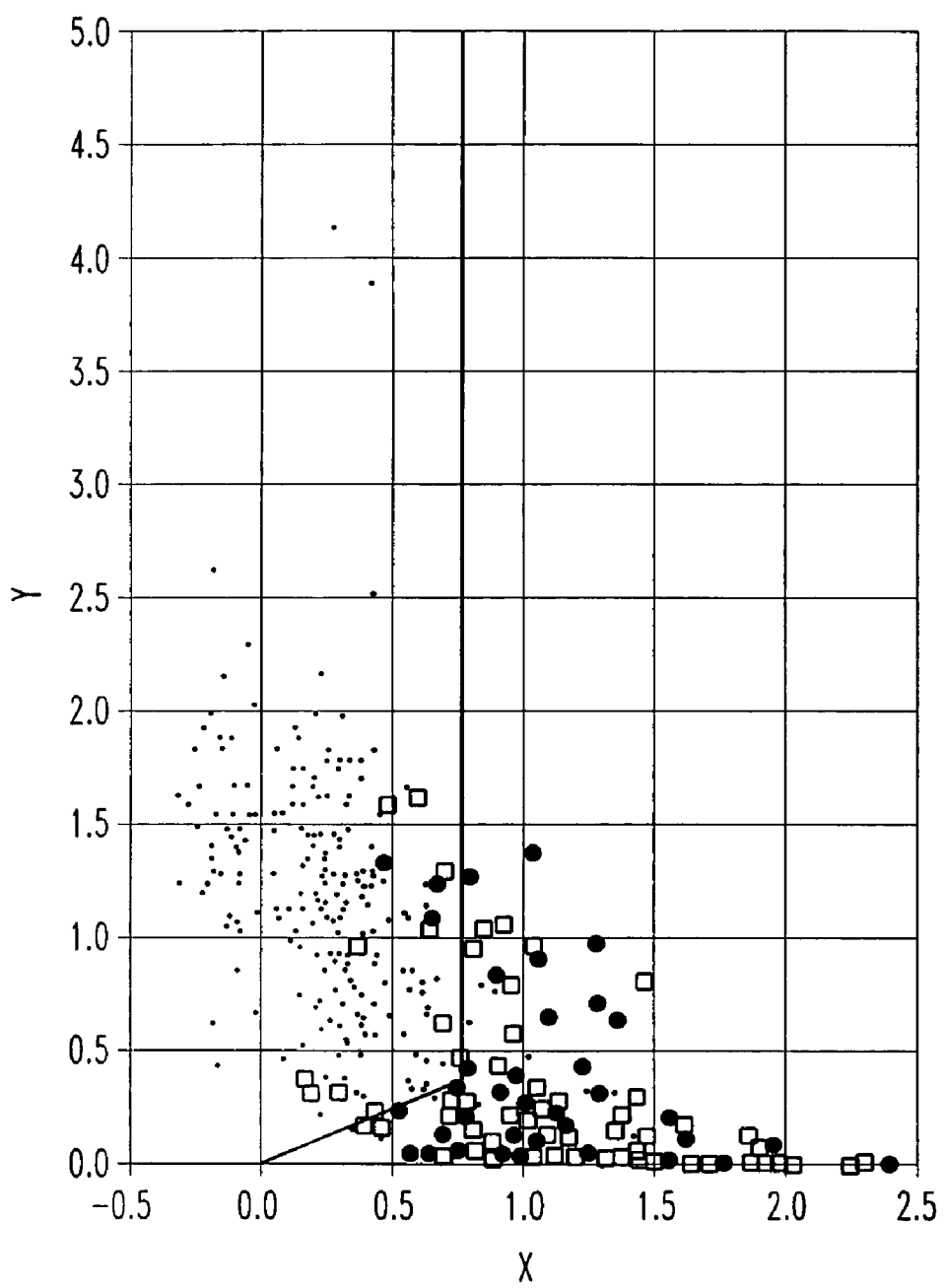
FIG. 7C is a histogram of individual cells as a function of X and Y values.

FIG. 7 . Tumor sample 3852. 7A, 7B, and 7C, as in FIG. 3.

FIG. 8. Tumor sample 3852. 8A) DNA histogram of entire sample, uncorrected, 8B) DNA histogram of the entire sample, corrected for aggregates with cell function only, 8C) DNA histogram of the entire sample corrected for aggregates with saddle function plus APT algorithm, 8D) same as 8C, but at higher ordinate magnification.

FIG. 9. Upper panels show saddle function/APT corrected DNA histograms of 5 "Diploid" tumors. Lower panels show saddle function/APT corrected DNA histograms of five normal sputum samples. In the upper panels the ratio of G 2 M cell fraction to the S fraction is greater than 1 in four of the five samples. In the lower panels the ratio of the G 2 M cell fraction to the S fraction is less than one in all samples.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

APPENDIX

TABLE 1

| A | B<br>Type | C<br>Cell # | D<br>Agg # (%) | E<br>Poat-$G_2M$ Singlets<br>Cell # (%) | F<br>[Octaploid +]Singlets<br>Cell # (%) |
|---|---|---|---|---|---|
| FLS | Normal Lymphocytes | 400 | 24 (6.0) | 1 (0.25) | 0 (0.0) |
| 362 | Normal Sputum | 400 | 71 (17.8) | 1 (0.25) | 0 (0.0) |
| 366 | Normal Sputum | 401 | 41 (10.2) | 1 (0.25) | 0 (0.0) |

TABLE 1-continued

| A | B<br>Type | C<br>Cell # | D<br>Agg # (%) | E<br>Post-G$_2$M Singlets<br>Cell # (%) | F<br>[Octaploid +]Singlets<br>Cell # (%) |
|---|---|---|---|---|---|
| 373 | Normal Sputum | 398 | 34 (8.5) | 0 (0.0) | 0 (0.0) |
| 437 | Normal Sputum | 400 | 73 (18.3) | 4 (1.0) | 0 (0.0) |
| 438 | Normal Sputum | 401 | 40 (10.0) | 3 (0.75) | 0 (0.0) |
| JC | Breast Cancer Cell Line | 400 | 94 (23.5) | 9 (2.3) | 1 (0.25) |
| MB231 | Breast Cancer Cell Line | 401 | 223 (55.6) | 24 (6.0) | 5 (1.2) |
| MB468 | Breast Cancer Cell Line | 400 | 48 (12.0) | 5 (1.3) | 2 (0.5) |
| MCF7 | Breast Cancer Cell Line | 399 | 111 (27.8) | 7 (1.8) | 0 (0.0) |
| SKBR3 | Breast Cancer Cell Line | 401 | 63 (15.7) | 10 (2.5) | 0 (0.0) |
| 3726 | Primary Breast Cancer | 402 | 87 (21.6) | 1 (0.25) | 0 (0.0) |
| 3655 | Primary Breast Cancer | 400 | 87 (21.8) | 102 (25.5) | 15 (3.8) |
| 3838 | Primary Breast Cancer | 405 | 77 (19.0) | 30 (7.4) | 7 (1.7) |
| 3815 | Primary Breast Cancer | 403 | 68 (16.9) | 11 (2.7) | 5 (1.2) |
| 3846 | Primary Breast Cancer | 401 | 105 (26.2) | 7 (1.7) | 1 (0.2) |
| 3819 | Primary Lung Cancer | 404 | 95 (23.5) | 32 (7.9) | 5 (1.2) |
| 3839 | Primary Lung Cancer | 404 | 52 (12.9) | 15 (3.7) | 1 (0.25) |
| 3841 | Primary Lung Cancer | 401 | 121 (30.2) | 3 (0.75) | 2 (0.50) |
| 3849 | Primary Lung Cancer | 335 | 41 (12.2) | 9 (2.7) | 2 (0.60) |
| 3852 | Primary Lung Cancer | 402 | 130 (32.3) | 44 (10.9) | 7 (1.7) |
| | Mean | 398 | 80.2 (20.1) | 15.2 (3.8) | 2.5 (0.6) |

TABLE 2

Saddle Function

| A | B<br>Total Agg. | C<br>False Pos | D<br>False Neg | E<br>True Pos | F<br>True Neg | G<br>Sensitivity (%) | H<br>Specificity (%) | I<br>Singlet Predictive Value (%) | J<br>Residual (%) |
|---|---|---|---|---|---|---|---|---|---|
| FLS | 21 | 1 | 4 | 20 | 375 | 83.33 | 99.73 | 98.94 | 1.06 |
| 362 | 55 | 5 | 21 | 50 | 324 | 70.42 | 98.48 | 93.91 | 6.09 |
| 366 | 28 | 3 | 16 | 25 | 357 | 60.98 | 99.17 | 95.71 | 4.29 |
| 373 | 26 | 0 | 8 | 26 | 364 | 76.47 | 100.00 | 97.85 | 2.15 |
| 437 | 62 | 12 | 23 | 50 | 315 | 68.49 | 96.33 | 93.20 | 6.80 |
| 438 | 31 | 4 | 13 | 27 | 357 | 67.50 | 98.89 | 96.49 | 3.51 |
| JC | 90 | 9 | 13 | 81 | 297 | 86.17 | 97.06 | 95.81 | 4.19 |
| MB231 | 198 | 9 | 34 | 189 | 169 | 84.75 | 94.94 | 83.25 | 16.75 |
| MB468 | 54 | 14 | 8 | 40 | 338 | 83.33 | 96.02 | 97.69 | 2.31 |
| MCF7 | 104 | 12 | 19 | 92 | 276 | 82.88 | 95.83 | 93.56 | 6.44 |
| SKBR3 | 58 | 9 | 14 | 49 | 329 | 77.78 | 97.34 | 95.92 | 4.08 |
| 3726 | 73 | 9 | 23 | 64 | 306 | 73.56 | 97.14 | 93.01 | 6.99 |
| 3655 | 76 | 7 | 18 | 69 | 306 | 79.31 | 97.76 | 94.44 | 5.56 |
| 3838 | 52 | 12 | 37 | 40 | 316 | 51.95 | 96.34 | 89.52 | 10.48 |
| 3815 | 43 | 7 | 32 | 36 | 328 | 52.94 | 97.91 | 91.11 | 8.89 |
| 3846 | 81 | 8 | 32 | 73 | 288 | 69.52 | 97.30 | 90.00 | 10.00 |
| 3819 | 84 | 19 | 30 | 65 | 290 | 68.42 | 93.85 | 90.63 | 9.38 |
| 3839 | 58 | 21 | 15 | 37 | 331 | 71.15 | 94.03 | 95.66 | 4.34 |
| 3841 | 100 | 8 | 29 | 92 | 272 | 76.03 | 97.14 | 90.37 | 9.63 |
| 3849 | 27 | 4 | 18 | 23 | 290 | 56.10 | 98.64 | 94.16 | 5.84 |
| 3852 | 97 | 7 | 40 | 90 | 265 | 69.23 | 97.43 | 86.89 | 13.11 |
| Mean | 67.52 | 8.57 | 21.29 | 58.95 | 309.19 | 71.92 | 97.21 | 93.24 | 6.76 |
| STDev | 39.47 | 5.26 | 10.16 | 38.05 | 44.56 | 10.16 | 1.68 | 3.85 | 3.85 |

TABLE 3

APT Algorithm

| A | B<br>Total Agg. | C<br>False Pos | D<br>False Neg | E<br>True Pos | F<br>True Neg | G<br>Sensitivity (%) | H<br>Specificity (%) | I<br>Singlet Predictive Value (%) | J<br>Residual (%) |
|---|---|---|---|---|---|---|---|---|---|
| FLS | 19 | 5 | 10 | 14 | 371 | 58.33 | 98.67 | 97.38 | 2.62 |
| 362 | 56 | 6 | 21 | 50 | 323 | 70.42 | 98.18 | 93.90 | 6.10 |
| 366 | 35 | 2 | 8 | 33 | 358 | 80.49 | 99.44 | 97.81 | 2.19 |
| 373 | 29 | 7 | 12 | 22 | 357 | 64.71 | 98.08 | 96.75 | 3.25 |
| 437 | 64 | 6 | 15 | 58 | 321 | 79.45 | 98.17 | 95.54 | 4.46 |
| 438 | 27 | 2 | 15 | 25 | 359 | 62.50 | 99.45 | 95.99 | 4.01 |
| JC | 69 | 5 | 30 | 64 | 301 | 68.09 | 98.37 | 90.94 | 9.06 |
| MB231 | 187 | 7 | 43 | 180 | 171 | 80.72 | 96.07 | 79.91 | 20.09 |
| MB468 | 36 | 1 | 13 | 35 | 351 | 72.92 | 99.72 | 96.43 | 3.57 |
| MCF7 | 81 | 4 | 34 | 77 | 284 | 69.37 | 98.61 | 89.31 | 10.69 |

TABLE 3-continued

APT Algorithm

| A | B Total Agg. | C False Pos | D False Neg | E True Pos | F True Neg | G Sensitivity (%) | H Specificity (%) | I Singlet Predictive Value (%) | J Residual (%) |
|---|---|---|---|---|---|---|---|---|---|
| SKBR3 | 48 | 6 | 21 | 42 | 332 | 66.67 | 98.22 | 94.05 | 5.95 |
| 3726 | 59 | 0 | 28 | 59 | 315 | 67.82 | 100.00 | 91.84 | 8.16 |
| 3655 | 89 | 22 | 20 | 67 | 291 | 77.01 | 92.97 | 93.57 | 6.43 |
| 3838 | 65 | 6 | 18 | 59 | 322 | 76.62 | 98.17 | 94.71 | 5.29 |
| 3815 | 58 | 11 | 21 | 47 | 324 | 69.12 | 96.72 | 93.91 | 6.09 |
| 3846 | 76 | 1 | 30 | 75 | 295 | 71.43 | 99.66 | 90.77 | 9.23 |
| 3819 | 112 | 32 | 15 | 80 | 277 | 84.21 | 89.64 | 94.86 | 5.14 |
| 3839 | 49 | 9 | 12 | 40 | 343 | 76.92 | 97.44 | 96.62 | 3.38 |
| 3841 | 102 | 5 | 24 | 97 | 275 | 80.17 | 98.21 | 91.97 | 8.03 |
| 3849 | 45 | 12 | 8 | 33 | 282 | 80.49 | 95.92 | 97.24 | 2.76 |
| 3852 | 153 | 31 | 8 | 122 | 241 | 93.85 | 88.60 | 96.79 | 3.21 |
| Mean | 69.48 | 8.57 | 19.33 | 60.90 | 309.19 | 73.87 | 97.16 | 93.82 | 6.18 |
| STDev | 41.51 | 8.99 | 9.45 | 37.71 | 46.40 | 8.30 | 3.11 | 4.01 | 4.01 |

TABLE 4

Combined Saddle Function APT Algorithm

| A | B Total Agg. | C False Pos | D False Neg | E True Pos | F True Neg | G Sensitivity (%) | H Specificity (%) | I Singlet Predictive Value (%) | J Residual (%) |
|---|---|---|---|---|---|---|---|---|---|
| FLS | 30 | 6 | 0 | 24 | 370 | 100.00 | 98.40 | 100.00 | 0.00 |
| 362 | 71 | 9 | 9 | 62 | 320 | 87.32 | 97.26 | 97.26 | 2.74 |
| 366 | 46 | 5 | 0 | 41 | 355 | 100.00 | 98.61 | 100.00 | 0.00 |
| 373 | 39 | 7 | 2 | 32 | 357 | 94.12 | 98.08 | 99.44 | 0.56 |
| 437 | 85 | 18 | 6 | 67 | 309 | 91.78 | 94.50 | 98.10 | 1.90 |
| 438 | 44 | 6 | 2 | 38 | 355 | 95.00 | 98.34 | 99.44 | 0.56 |
| JC | 103 | 14 | 5 | 89 | 292 | 94.68 | 95.42 | 98.32 | 1.68 |
| MB231 | 223 | 13 | 13 | 210 | 165 | 94.17 | 92.70 | 92.70 | 7.30 |
| MB468 | 58 | 15 | 5 | 43 | 337 | 89.58 | 95.74 | 98.54 | 1.46 |
| MCF7 | 116 | 16 | 11 | 100 | 272 | 90.09 | 94.44 | 96.11 | 3.89 |
| SKBR3 | 69 | 13 | 7 | 56 | 325 | 88.89 | 96.15 | 97.89 | 2.11 |
| 3726 | 84 | 9 | 12 | 75 | 306 | 86.21 | 97.14 | 96.23 | 3.77 |
| 3655 | 108 | 27 | 6 | 81 | 286 | 93.10 | 91.37 | 97.95 | 2.05 |
| 3838 | 86 | 18 | 9 | 68 | 310 | 88.31 | 94.51 | 97.18 | 2.82 |
| 3815 | 70 | 17 | 15 | 53 | 318 | 77.94 | 94.93 | 95.50 | 4.50 |
| 3846 | 97 | 9 | 17 | 88 | 287 | 83.81 | 96.96 | 94.41 | 5.59 |
| 3819 | 131 | 42 | 6 | 89 | 267 | 93.68 | 86.41 | 97.80 | 2.20 |
| 3839 | 80 | 29 | 1 | 51 | 323 | 98.08 | 91.76 | 99.69 | 0.31 |
| 3841 | 126 | 13 | 8 | 113 | 267 | 93.39 | 95.36 | 97.09 | 2.91 |
| 3849 | 50 | 15 | 6 | 35 | 279 | 85.37 | 94.90 | 97.89 | 2.11 |
| 3852 | 162 | 35 | 3 | 127 | 237 | 97.69 | 87.13 | 98.75 | 1.25 |
| Mean | 89.43 | 16.00 | 6.81 | 73.43 | 301.76 | 91.58 | 94.77 | 97.63 | 2.37 |
| STDev | 45.45 | 9.79 | 4.80 | 41.74 | 46.70 | 5.58 | 3.36 | 1.86 | 1.86 |

TABLE 5

| | | | All Cells | G1S | G2M | Hypertetraploid | Octaploid+ |
|---|---|---|---|---|---|---|---|
| 1 | A | Total Cells | 398.0 | 293.6 | 31.7 | 36.0 | 36.8 |
| 2 | B | Original Singlets | 317.8 | 285.8 | 16.8 | 12.7 | 2.5 |
| 3 | C | Total Recovered | 308.6 | 277.3 | 18.1 | 11.6 | 1.6 |
| 4 | D | Singlets Recovered | 301.9 | 276.0 | 15.3 | 9.4 | 1.2 |
| 5 | B/A | original singlet purity | 0.798 | 0.974 | 0.529 | 0.352 | 0.069 |
| 6 | D/C | final singlet purity | 0.978 | 0.995 | 0.845 | 0.811 | 0.735 |
| 7 | D/B | Singlet Yield | 0.950 | 0.966 | 0.915 | 0.741 | 0.472 |
| 8 | C/B | Expected Yield Ratio | 0.971 | 0.970 | 1.082 | 0.914 | 0.642 |

TABLE 6

| A "Diploid Tumors | B<br>% S/Model | C<br>% "G$_2$M"/Model | D<br>"G$_2$M"/S Ratio | E<br>% Agg/Model | F<br>% Agg/Visual | G<br>"G$_2$M" Purity | H<br>Expected<br>Yield Ratio |
|---|---|---|---|---|---|---|---|
| 3726 | 1.3 | 5.2 | 4.0 | 1.9 | 3.8 | 0.62 | 1.63 |
| 3838 | 21.2 | 16.0 | 0.8 | 5.4 | 2.8 | 0.88 | 1.04 |
| 3846 | 2.9 | 5.0 | 1.7 | 3.8 | 5.6 | 0.58 | 1.71 |
| 3819 | 7.9 | 17.2 | 2.2 | 2.9 | 1.8 | 0.96 | 0.65 |
| 3841 | 3.1 | 7.4 | 2.4 | 6.2 | 2.9 | 0.68 | 1.46 |
| mean | 7.28 | 10.16 | 2.21 | 4.04 | 3.38 | 0.74 | 1.30 |
| Sputum Samples | | | | | | | |
| 362 | 4.2 | 1.8 | 0.4 | 0.8 | 2.7 | 0.8 | 1.2 |
| 366 | 8.4 | 0 | 0.0 | 0.7 | 0 | 1.0 | 1.0 |
| 373 | 2.7 | 0.3 | 0.1 | 0.3 | 0.6 | 0.5 | 2.0 |
| 437 | 6.1 | 0 | 0.0 | 0.3 | 1.9 | 0.3 | 4.0 |
| 438 | 3.1 | 2.1 | 0.7 | 0.5 | 0.6 | 1.0 | 1.0 |
| mean | 4.9 | 0.84 | 0.24 | 0.52 | 1.16 | 0.72 | 1.84 |

What is claimed is:

1. A method for correcting for cell aggregates in a cell suspension from patients comprising the steps of:

obtaining samples of cells from the cell suspension;
scanning by laser cytometry the samples;
storing data about the samples;
identifying in the data cell aggregates in the samples from the samples that have been scanned with an APT function defined by $X = \log(\text{normalized nuclear area} \times \text{normalized nuclear perimeter})$, where normalized nuclear area cell=cell nuclear area/mean nuclear area of G1 cells with a lowest ploidy level in the sample, and normalized nuclear perimeter=cell nuclear perimeter/mean nuclear perimeter of G1 cells with the lowest ploidy level in the sample; and $Y = 1/(\text{normalized texture value})$, where normalized texture value=cell texture value/mean cell texture value of G1 cells with the lowest ploidy level in the sample according to a heuristic:

for $X < 0.75, Y < 0.5X$, and, for $X \geq 0.75$, all Y.

2. A method as described in claim 1 including the step of removing cell aggregates from the data.

3. A method as described in claim 2 including the step of staining cells in the samples.

4. A method as described in claim 3 wherein the identifying aggregates with an APT function includes the step of forming a product from the data of the sample of a cell nuclear area and the cell perimeter normalized with respect to cell singlets from the sample.

5. A method as described in claim 4 wherein the identifying aggregates with an APT function includes the step of measuring the cell texture.

6. A method as described in claim 5 wherein the measuring step includes the step of identifying cell wedges in an intercellular region of a nuclear silhouette in the data of the sample.

7. A method as described in claim 4 wherein the identifying aggregates in the data with a saddle function step includes the step of identifying in the data of a sample the brightest pixel and a next brightest pixel, and determining that there are at least a plurality of pixels between the brightest pixel and the next brightest pixel.

* * * * *